US006268053B1

(12) United States Patent
Woiszwillo et al.

(10) Patent No.: US 6,268,053 B1
(45) Date of Patent: *Jul. 31, 2001

(54) MACROMOLECULAR MICROPARTICLES AND METHODS OF PRODUCTION AND USE

(75) Inventors: James E. Woiszwillo, Milford; Larry R. Brown, Newton; Terrence L. Scott, Winchester; Jie Di, Norwood; Judith Sudhalter, Newton; Charles D. Blizzard, Roxbury; Frank J. Riske, Stoughton, all of MA (US)

(73) Assignee: Epic Therapeutics, Inc., Norwood, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/483,657

(22) Filed: Jan. 14, 2000

Related U.S. Application Data

(63) Continuation of application No. 08/699,586, filed on Aug. 19, 1996, now Pat. No. 6,090,925, which is a continuation-in-part of application No. 08/206,456, filed on Mar. 4, 1994, now Pat. No. 5,578,709, which is a continuation-in-part of application No. 08/028,237, filed on Mar. 9, 1993, now abandoned.

(51) Int. Cl.[7] .................................................... B32B 15/02
(52) U.S. Cl. ........................ 428/402; 436/523; 436/528; 530/350; 530/402
(58) Field of Search .................................. 428/327, 402; 436/523, 528; 530/350, 402, 812, 815

(56) References Cited

U.S. PATENT DOCUMENTS

| Re. 33,670 | 8/1991 | Maglio | 424/408 |
|---|---|---|---|
| Re. 35,862 | 7/1998 | Steiner et al. | 424/455 |
| 2,489,763 | 11/1949 | Dunne | 530/373 |
| 2,628,227 | 2/1953 | Ames | 530/380 |
| 2,831,767 | 4/1958 | Dann et al. | 430/628 |
| 3,088,875 | 5/1963 | Fisk | 436/509 |
| 3,089,818 | 5/1963 | Stone | 525/54 |
| 3,137,631 | 6/1964 | Soloway | 424/491 |
| 3,242,051 | 3/1966 | Hiestand et al. | 427/214 |
| 3,317,434 | 5/1967 | Veis et al. | 247/213 |
| 3,336,155 | 8/1967 | Rowe | 427/212 |
| 3,341,466 | 9/1967 | Brynko et al. | 427/213 |
| 3,407,076 | 10/1968 | Ganz | 426/570 |
| 3,510,435 | 5/1970 | Sirine | 585/419 |
| 3,616,229 | 10/1971 | Wildi et al. | 435/175 |
| 3,619,371 | 11/1971 | Crook et al. | 435/179 |
| 3,663,687 | 5/1972 | Evans | 424/1 |
| 3,664,963 | 5/1972 | Pasin | 427/213 |
| 3,679,653 | 7/1972 | Schuck et al. | 525/54 |
| 3,691,090 | 9/1972 | Kitajima et al. | 427/213 |
| 3,694,372 | 9/1972 | Anderson et al. | 428/402 |
| 3,703,474 | 11/1972 | Huber | 264/4 |
| 3,743,604 | 7/1973 | Schnoring et al. | 427/213 |
| 3,764,477 | 10/1973 | Klaus et al. | 435/180 |

(List continued on next page.)

FOREIGN PATENT DOCUMENTS

| 2149736 | 4/1972 | (DE) . |
|---|---|---|
| 03916020A1 | 11/1990 | (DE) . |
| 04121820A1 | 1/1993 | (DE) . |
| 04122591C1 | 2/1993 | (DE) . |
| 04312970A1 | 10/1994 | (DE) . |
| 0 009 842A1 | 9/1979 | (EP) . |
| 00052510A2 | 5/1982 | (EP) . |
| 0009366A1 | 11/1983 | (EP) . |
| 00097907A2 | 1/1984 | (EP) . |
| 0 106 495 | 4/1984 | (EP) . |
| 0 106 495 A3 | 4/1984 | (EP) . |
| 00135129A2 | 3/1985 | (EP) . |
| 0 173 928 B1 | 8/1985 | (EP) . |
| 0 052 510 B1 | 8/1986 | (EP) . |
| 0 190 833 A2 | 8/1986 | (EP) . |
| 0 202 065 A2 | 11/1986 | (EP) . |
| 0248531 A2 | 5/1987 | (EP) . |
| 00288737A1 | 11/1988 | (EP) . |
| 00293172A2 | 11/1988 | (EP) . |
| 00295968A1 | 12/1988 | (EP) . |
| 00302582A1 | 2/1989 | (EP) . |
| 00325359A1 | 7/1989 | (EP) . |
| 00350246A2 | 1/1990 | (EP) . |
| 0 357 401 | 3/1990 | (EP) . |

(List continued on next page.)

OTHER PUBLICATIONS

"Immobilization of Thermostable .alpha.–Galactosidase from Pycnoporus cinnabarinus on Chitosan Beads and Its Application to the Hydrolysis of Raffinose in Beet Sugar Molasses"; Ohtakara et al.: J. Ferment Technol., vol. 65, No. 4, pp. 493–498; 1987.

"The Controlled parenteral delivery of polypeptides and proteins"; C.G. Pitt; International Journal of Pharmaceutics; 59 (1990); pp. 173–196.

Harris, W.J. and Emery, S., "Therapeutic Antibodies—The Coming of Age", Tib Tech, vol. 11, pp. 42–44.

Farrugia, et al., "Studies on the Procurement of Coagulation Factor VIII: Selective Precipitation of Factor VII with Hydrophilic Polymers", Thromb. Haemostas, 51(3), pp. 338–342, (1984).

Suelter, C. H., "A Practice Guide to Enzymology", John Wiley & Sons, pp. 78–87, (1986).

Taylor, R., "Expanding Applications in the Food Industry for Immobilized Enzymes", Genetic Eng. News, p. 5, (Feb. 1993).

Danishefsky, S., "Catalytic Antibodies and Disfavored Reactions", Science, 259, pp. 469–470, (1993).

(List continued on next page.)

Primary Examiner—H. Thi Le
(74) Attorney, Agent, or Firm—Wolf, Greenfield & Sacks, P.C.

(57) ABSTRACT

Methods relating to the field of biochemistry and more specifically relating to microparticles for use in diagnostics, therapeutics, and research are provided.

10 Claims, 5 Drawing Sheets

U.S. PATENT DOCUMENTS

| | | | |
|---|---|---|---|
| 3,775,253 | 11/1973 | Dieter et al. | 435/180 |
| 3,775,378 | 11/1973 | Dahlmans et al. | 525/54 |
| 3,838,007 | 9/1974 | van Velzen | 435/965 |
| 3,857,931 | 12/1974 | Hager | 436/509 |
| 3,871,888 | 3/1975 | Michel-Wolwertz et al. | 430/495 |
| 3,871,964 | 3/1975 | Huper et al. | 435/44 |
| 4,011,205 | 3/1977 | Dean et al. | 530/405 |
| 4,035,316 | 7/1977 | Yen et al. | 521/65 |
| 4,038,140 | 7/1977 | Jaworek et al. | 435/178 |
| 4,039,413 | 8/1977 | Kraemer et al. | 522/13 |
| 4,046,722 | 9/1977 | Rowland | 530/362 |
| 4,061,466 | 12/1977 | Sjoholm et al. | 436/535 |
| 4,064,080 | 12/1977 | Daniel | 542/575 |
| 4,070,348 | 1/1978 | Kraemer et al. | 526/273 |
| 4,094,744 | 6/1978 | Hartdegen et al. | 435/182 |
| 4,105,598 | 8/1978 | Yen et al. | 521/53 |
| 4,107,288 | 8/1978 | Oppenheim et al. | 424/499 |
| 4,115,534 | 9/1978 | Ithakissios | 436/500 |
| 4,116,949 | 9/1978 | Goodman et al | 525/54 |
| 4,118,349 | 10/1978 | Bonacker et al. | 525/54 |
| 4,138,356 | 2/1979 | Vincent et al. | 252/182 |
| 4,138,383 | 2/1979 | Rembaum et al. | 524/809 |
| 4,144,050 | 3/1979 | Frensch et al. | 504/192 |
| 4,147,767 | 4/1979 | Yapel, Jr. | 424/499 |
| 4,157,437 | 6/1979 | Okuzumi et al. | 528/354 |
| 4,166,105 | 8/1979 | Hirschfeld | 436/536 |
| 4,169,804 | 10/1979 | Yapel | 252/62 |
| 4,181,636 | 1/1980 | Fischer | 525/54 |
| 4,184,986 | 1/1980 | Krasnobajew et al. | 525/54 |
| 4,210,723 | 7/1980 | Dorman et al. | 435/180 |
| 4,224,198 | 9/1980 | Rembaum et al. | 525/54 |
| 4,256,737 | 3/1981 | Nestor et al. | 514/6 |
| 4,267,234 | 5/1981 | Rembaum | 428/403 |
| 4,267,235 | 5/1981 | Rembaum et al. | 428/407 |
| 4,277,364 | 7/1981 | Shasha et al. | 504/244 |
| 4,322,311 | 3/1982 | Lim et al. | 264/4 |
| 4,326,008 | 4/1982 | Rembaum | 428/403 |
| 4,344,857 | 8/1982 | Shasha et al. | 504/244 |
| 4,349,530 | 9/1982 | Royer | 424/426 |
| 4,353,962 | 10/1982 | Himel et al. | 428/407 |
| 4,357,259 | 11/1982 | Senyei et al. | 264/4 |
| 4,359,377 | 11/1982 | Blanc et al. | 204/279 |
| 4,377,567 | 3/1983 | Geho | 424/1 |
| 4,382,813 | 5/1983 | Shasha | 504/220 |
| 4,389,330 | 6/1983 | Tice et al. | 427/213 |
| 4,391,309 | 7/1983 | Steiner | 141/18 |
| 4,407,957 | 10/1983 | Lim | 435/178 |
| 4,421,896 | 12/1983 | Dorman | 525/54 |
| 4,438,239 | 3/1984 | Rembaum et al. | 525/54 |
| 4,439,488 | 3/1984 | Trimnell et al. | 428/402 |
| 4,460,722 | 7/1984 | Igarashi et al. | 523/206 |
| 4,472,382 | 9/1984 | Labrie et al. | 514/15 |
| 4,482,606 | 11/1984 | Bousquet et al. | 428/402 |
| 4,490,407 | 12/1984 | Lafon | 427/2 |
| 4,495,288 | 1/1985 | Jarvis, Jr. et al. | 435/382 |
| 4,496,689 | 1/1985 | Mitra | 525/54 |
| 4,511,694 | 4/1985 | Kramer et al. | 525/54 |
| 4,522,812 | 6/1985 | Koguchi et al. | 514/7 |
| 4,526,938 | 7/1985 | Churchill et al. | 525/415 |
| 4,530,840 | 7/1985 | Tice et al. | 514/179 |
| 4,540,602 | 9/1985 | Motoyama et al. | 427/213 |
| 4,552,812 | 11/1985 | Margel et al. | 428/407 |
| 4,590,068 | 5/1986 | Berthet et al. | 514/282 |
| 4,605,550 | 8/1986 | Trill | 424/487 |
| 4,606,940 | 8/1986 | Frank et al. | 427/213 |
| 4,608,277 | 8/1986 | Greiner et al. | 427/213 |
| 4,608,278 | 8/1986 | Frank et al. | 427/213 |
| 4,609,707 | 9/1986 | Nowinski et al. | 525/54 |
| 4,613,500 | 9/1986 | Suzuki et al. | 424/85 |
| 4,617,186 | 10/1986 | Schafer et al. | 424/78 |
| 4,622,244 | 11/1986 | Lapka et al. | 427/213 |
| 4,622,362 | 11/1986 | Rembaum | 525/54 |
| 4,637,480 | 1/1987 | Obrecht et al. | 340/853 |
| 4,642,111 | 2/1987 | Sakamoto et al. | 424/492 |
| 4,645,664 | 2/1987 | Lange | 514/772 |
| 4,652,441 | 3/1987 | Okada et al. | 424/497 |
| 4,666,641 | 5/1987 | Fickat et al. | 264/4 |
| 4,671,954 | 6/1987 | Goldberg et al. | 424/1 |
| 4,674,480 | 6/1987 | Lemelson | 424/1 |
| 4,675,189 | 6/1987 | Kent et al. | 424/490 |
| 4,677,191 | 6/1987 | Tanaka et al. | 528/361 |
| 4,690,906 | 9/1987 | Duheille et al. | 435/5 |
| 4,708,816 | 11/1987 | Chang et al. | 2582/186 |
| 4,713,249 | 12/1987 | Schroder | 424/1 |
| 4,727,064 | 2/1988 | Pitha | 514/58 |
| 4,728,640 | 3/1988 | Labrie et al. | 514/15 |
| 4,744,178 | 5/1988 | Afshar | 451/438 |
| 4,744,933 | 5/1988 | Rha et al. | 264/4.3 |
| 4,745,102 | 5/1988 | Labrie et al. | 514/15 |
| 4,752,638 | 6/1988 | Nowinski et al. | 525/54 |
| 4,761,398 | 8/1988 | Edens et al. | 514/15 |
| 4,764,467 | 8/1988 | Goertz et al. | 435/182 |
| 4,766,012 | 8/1988 | Valenti | 427/213 |
| 4,775,660 | 10/1988 | Labrie et al. | 514/15 |
| 4,777,089 | 10/1988 | Takizawa et al. | 428/402 |
| 4,783,335 | 11/1988 | Lipshitz | 424/407 |
| 4,783,336 | 11/1988 | Margel et al. | 424/462 |
| 4,794,000 | 12/1988 | Ecanow | 424/457 |
| 4,795,641 | 1/1989 | Kashdan | 424/438 |
| 4,801,529 | 1/1989 | Perlman | 435/5 |
| 4,812,445 | 3/1989 | Eden et al. | 514/60 |
| 4,818,542 | 4/1989 | DeLuca et al. | 424/491 |
| 4,822,534 | 4/1989 | Lencki et al. | 264/4 |
| 4,822,535 | 4/1989 | Ekman et al. | 264/4 |
| 4,824,678 | 4/1989 | Lindahl et al. | 424/473 |
| 4,826,689 | 5/1989 | Violanto et al. | 424/489 |
| 4,832,686 | 5/1989 | Anderson | 604/500 |
| 4,849,228 | 7/1989 | Yamamoto et al. | 424/457 |
| 4,851,386 | 7/1989 | Labrie et al. | 514/15 |
| 4,853,226 | 8/1989 | Machida et al. | 424/426 |
| 4,863,729 | 9/1989 | Zuckerandl | 424/85 |
| 4,863,972 | 9/1989 | Itagaki et al. | 521/141 |
| 4,865,846 | 9/1989 | Kaufman | 424/428 |
| 4,865,850 | 9/1989 | Shell et al. | 424/491 |
| 4,871,716 | 10/1989 | Longo et al. | 514/2 |
| 4,882,166 | 11/1989 | Graham et al. | 424/462 |
| 4,895,724 | 1/1990 | Cardinal et al. | 424/418 |
| 4,897,267 | 1/1990 | Bontemps et al. | 424/422 |
| 4,897,268 | 1/1990 | Tice et al. | 424/422 |
| 4,904,479 | 2/1990 | Illum | 424/490 |
| 4,904,592 | 2/1990 | Freeman et al. | 435/183 |
| 4,906,488 | 3/1990 | Pera | 426/573 |
| 4,908,233 | 3/1990 | Takizawa et al. | 427/213 |
| 4,911,952 | 3/1990 | Doane et al. | 427/213 |
| 4,913,908 | 4/1990 | Couvreur et al. | 424/501 |
| 4,917,893 | 4/1990 | Okada et al. | 424/423 |
| 4,923,645 | 5/1990 | Tsang et al. | 264/4 |
| 4,925,673 | 5/1990 | Steiner et al. | 424/455 |
| 4,925,677 | 5/1990 | Feijen | 424/484 |
| 4,931,284 | 6/1990 | Ekman et al. | 424/450 |
| 4,931,362 | 6/1990 | Zsifkovits et al. | 428/402 |
| 4,933,185 | 6/1990 | Wheatley et al. | 424/461 |
| 4,935,172 | 6/1990 | Ishiguro et al. | 264/4 |
| 4,938,797 | 7/1990 | Hasslin et al. | 504/116 |
| 4,938,900 | 7/1990 | Moriwaki et al. | 264/4 |
| 4,954,298 | 9/1990 | Yamamoto et al. | 264/4 |
| 4,956,129 | 9/1990 | Scher et al. | 264/4 |
| 4,963,367 | 10/1990 | Ecanow | 424/485 |
| 4,963,526 | 10/1990 | Ecanow | 514/3 |
| 4,970,031 | 11/1990 | Gotoh | 264/4 |
| 4,973,469 | 11/1990 | Mulligan et al. | 424/461 |

| Patent No. | Date | Inventor | Class |
|---|---|---|---|
| 4,981,842 | 1/1991 | Labrie et al. | 514/15 |
| 4,985,064 | 1/1991 | Redlich et al. | 504/352 |
| 4,990,280 | 2/1991 | Thorengaard et al. | 510/301 |
| 4,997,454 | 3/1991 | Violante et al. | 23/305 |
| 5,008,116 | 4/1991 | Cahn | 424/491 |
| 5,008,117 | 4/1991 | Calanchi et al. | 424/494 |
| 5,019,370 | 5/1991 | Jay et al. | 424/4 |
| 5,019,400 | 5/1991 | Gombotz | 424/497 |
| 5,021,248 | 6/1991 | Stark et al. | 426/96 |
| 5,028,430 | 7/1991 | Sanders et al. | 424/423 |
| 5,034,217 | 7/1991 | DeFrossez et al. | 424/64 |
| 5,041,292 | 8/1991 | Feijen | 424/484 |
| 5,049,322 | 9/1991 | Devissaguet et al. | 264/4 |
| 5,051,304 | 9/1991 | David et al. | 428/402 |
| 5,051,362 | 9/1991 | Suehiro et al. | 435/182 |
| 5,063,059 | 11/1991 | Ohtsubo et al. | 424/408 |
| 5,069,936 | 12/1991 | Yen | 427/213 |
| 5,073,365 | 12/1991 | Katz et al. | 424/489 |
| 5,075,109 | 12/1991 | Tice et al. | 424/193 |
| 5,077,058 | 12/1991 | Lapoiriere et al. | 424/501 |
| 5,084,278 | 1/1992 | Mehta | 424/441 |
| 5,084,287 | 1/1992 | Ghebre-Sellassie et al. | 424/495 |
| 5,089,272 | 2/1992 | Shioya et al. | 424/493 |
| 5,089,407 | 2/1992 | Baker et al. | 435/179 |
| 5,093,198 | 3/1992 | Speaker et al. | 428/402 |
| 5,100,669 | 3/1992 | Hyon et al. | 424/426 |
| 5,100,753 | 3/1992 | Maniar et al. | 430/137 |
| 5,102,872 | 4/1992 | Singh et al. | 514/21 |
| 5,108,759 | 4/1992 | Ranney | 424/493 |
| 5,118,528 | 6/1992 | Fessi et al. | 427/213 |
| 5,120,349 | 6/1992 | Stewart et al. | 504/234 |
| 5,122,600 | 6/1992 | Kawaguchi et al. | 536/23 |
| 5,130,171 | 7/1992 | Prud'Homme et al. | 427/213 |
| 5,133,908 | 7/1992 | Stainmesse et al. | 264/7 |
| 5,141,738 | 8/1992 | Rasor et al. | 424/9 |
| 5,143,661 | 9/1992 | Lawter et al. | 264/4 |
| 5,149,543 | 9/1992 | Cohen et al. | 424/499 |
| 5,151,272 | 9/1992 | Engstrom et al. | 424/450 |
| 5,156,842 | 10/1992 | Mulligan | 424/195 |
| 5,160,745 | 11/1992 | Deluca et al. | 424/487 |
| 5,169,754 | 12/1992 | Siiman et al. | 435/5 |
| 5,178,882 | 1/1993 | Kossovsky et al. | 424/494 |
| 5,183,690 | 2/1993 | Carr et al. | 427/213 |
| 5,187,150 | 2/1993 | Speiser et al. | 514/2 |
| 5,189,021 | 2/1993 | Labrie et al. | 514/15 |
| 5,192,552 | 3/1993 | Fekete et al. | 424/4 |
| 5,192,741 | 3/1993 | Orsolini et al. | 514/4 |
| 5,204,108 | 4/1993 | Illum | 424/434 |
| 5,211,952 | 5/1993 | Spicer et al. | 424/426 |
| 5,213,788 | 5/1993 | Ranney | 424/9 |
| 5,213,812 | 5/1939 | Ruiz | 424/499 |
| 5,219,577 | 6/1993 | Kossovsky et al. | 424/494 |
| 5,223,263 | 6/1993 | Hostetler et al. | 424/450 |
| 5,232,707 | 8/1993 | Lokensgard | 424/490 |
| 5,238,714 | 8/1993 | Wallace et al. | 427/213 |
| 5,252,337 | 10/1993 | Powell | 424/456 |
| 5,252,459 | 10/1993 | Tarcha et al. | 435/6 |
| 5,264,618 | 11/1993 | Felgner et al. | 560/244 |
| 5,271,945 | 12/1993 | Yoshioka et al. | 424/489 |
| 5,271,961 | 12/1993 | Mathiowitz et al. | 427/213 |
| 5,275,820 | 1/1994 | Chang | 424/426 |
| 5,277,979 | 1/1994 | Kielbania, Jr. et al. | 428/402 |
| 5,284,881 | 2/1994 | Mizuguchi et al. | 521/57 |
| 5,286,489 | 2/1994 | Tsau et al. | 424/440 |
| 5,288,502 | 2/1994 | McGinity et al. | 424/484 |
| 5,292,512 | 3/1994 | Schaefer | 424/401 |
| 5,292,533 | 3/1994 | McMahon et al. | 424/408 |
| 5,296,228 | 3/1994 | Chang et al. | 424/422 |
| 5,298,410 | 3/1994 | Phillips et al. | 435/188 |
| 5,302,397 | 4/1994 | Amsden et al. | 424/476 |
| 5,302,401 | 4/1994 | Liversidge et al. | 424/501 |
| 5,316,774 | 5/1994 | Eury et al. | 424/501 |
| 5,320,840 | 6/1994 | Camble et al. | 424/85 |
| 5,326,692 | 7/1994 | Brinkley et al. | 435/6 |
| 5,328,695 | 7/1994 | Lucas et al. | 424/426 |
| 5,330,767 | 7/1994 | Yamamoto et al. | 424/497 |
| 5,330,768 | 7/1994 | Park et al. | 424/501 |
| 5,334,640 | 8/1994 | Desai et al. | 524/56 |
| 5,340,585 | 8/1994 | Pike et al. | 424/426 |
| 5,342,626 | 8/1994 | Winston, Jr. et al. | 424/461 |
| 5,350,741 | 9/1994 | Takada | 514/3 |
| 5,352,459 | 10/1994 | Hollister et al. | 424/489 |
| 5,356,617 | 10/1994 | Schlossman | 424/63 |
| 5,359,030 | 10/1994 | Ekwuribe | 530/303 |
| 5,360,610 | 11/1994 | Tice et al. | 424/426 |
| 5,366,733 | 11/1994 | Brizzolara et al. | 424/426 |
| 5,366,881 | 11/1994 | Singh et al | 435/177 |
| 5,380,536 | 1/1995 | Hubbell et al. | 424/497 |
| 5,384,124 | 1/1995 | Courteille et al. | 424/430 |
| 5,384,133 | 1/1995 | Boyes et al. | 424/501 |
| 5,384,333 | 1/1995 | Davis et al. | 514/772 |
| 5,385,738 | 1/1995 | Yamahira et al. | 424/489 |
| 5,389,613 | 2/1995 | Labrie et al. | 514/15 |
| 5,411,730 | 5/1995 | Kirpotin et al. | 424/322 |
| 5,413,797 | 5/1995 | Khan | 424/489 |
| 5,417,982 | 5/1995 | Modi | 424/486 |
| 5,417,986 | 5/1995 | Reid et al. | 424/499 |
| 5,418,010 | 5/1995 | Janda et al. | 427/213 |
| 5,422,120 | 6/1995 | Kim | 424/450 |
| 5,424,076 | 6/1995 | Gorissen et al. | 424/501 |
| 5,427,778 | 6/1995 | Finkenaur et al. | 424/78 |
| 5,429,824 | 7/1995 | June | 424/489 |
| 5,438,040 | 8/1995 | Ekwuribe | 514/3 |
| 5,439,688 | 8/1995 | Orsolini et al. | 424/489 |
| 5,443,841 | 8/1995 | Milstein et al. | 424/451 |
| 5,445,832 | 8/1995 | Orsolini et al. | 424/491 |
| 5,447,728 | 9/1995 | Milstein et al. | 424/490 |
| 5,451,410 | 9/1995 | Milstein et al. | 424/490 |
| 5,453,368 | 9/1995 | Tresco et al. | 435/182 |
| 5,460,830 | 10/1995 | Kossovsky et al. | 424/493 |
| 5,460,831 | 10/1995 | Kossovsky et al. | 424/493 |
| 5,462,750 | 10/1995 | Kossovsky et al. | 424/493 |
| 5,462,751 | 10/1995 | Kossovsky et al. | 424/494 |
| 5,468,505 | 11/1995 | Hubbell et al. | 424/484 |
| 5,470,512 | 11/1995 | Noji et al. | 264/4 |
| 5,470,582 | 11/1995 | Supersaxo et al. | 424/489 |
| 5,476,663 | 12/1995 | Okada et al. | 424/423 |
| 5,478,564 | 12/1995 | Wantier et al. | 424/426 |
| 5,480,656 | 1/1996 | Okada et al. | 424/493 |
| 5,480,790 | 1/1996 | Tischer et al. | 435/188 |
| 5,482,706 | 1/1996 | Igari et al. | 424/85 |
| 5,484,609 | 1/1996 | Ko | 424/470 |
| 5,484,894 | 1/1996 | Woiszwillo | 530/410 |
| 5,487,895 | 1/1996 | Dapper | 424/278 |
| 5,489,401 | 2/1996 | Freeman | 264/4 |
| 5,514,670 | 5/1996 | Friedman et al. | 514/2 |
| 5,516,531 | 5/1996 | Makino et al. | 424/494 |
| 5,525,519 | 6/1996 | Woiszwillo | 436/88 |
| 5,529,914 | 6/1996 | Hubbell et al. | 435/182 |
| 5,529,915 | 6/1996 | Phillips et al. | 435/188 |
| 5,534,269 | 7/1996 | Igari et al. | 424/489 |
| 5,540,937 | 7/1996 | Billot et al. | 424/489 |
| 5,543,158 | 8/1996 | Gref et al. | 424/501 |
| 5,543,332 | 8/1996 | Lihme et al. | 436/528 |
| 5,543,390 | 8/1996 | Yatvin et al. | 514/2 |
| 5,543,391 | 8/1996 | Yatvin et al. | 514/2 |
| 5,550,178 | 8/1996 | Desai et al. | 524/6 |
| 5,554,388 | 9/1996 | Illum | 424/501 |
| 5,554,730 | 9/1996 | Woiszwillo et al. | 530/410 |
| 5,556,583 | 9/1996 | Tashiro et al. | 264/4 |
| 5,565,215 | 10/1996 | Gref et al. | 424/501 |
| 5,567,435 | 10/1996 | Hubbell et al. | 424/426 |

| | | | | | | | |
|---|---|---|---|---|---|---|---|
| 5,569,467 | 10/1996 | Ruiz | 424/489 | 5,750,147 | 5/1998 | Kantor | 424/491 |
| 5,569,468 | 10/1996 | Modi | 424/491 | 5,753,234 | 5/1998 | Lee et al. | 424/204 |
| 5,573,909 | 11/1996 | Singer et al. | 435/6 | 5,759,551 | 6/1998 | Ladd et al. | 424/198 |
| 5,573,934 | 11/1996 | Hubbell | 435/177 | 5,759,582 | 6/1998 | Leong et al. | 424/492 |
| 5,574,011 | 11/1996 | Tien | 514/14 | 5,760,000 | 6/1998 | Habibi | 514/15 |
| 5,575,987 | 11/1996 | Kamei et al. | 424/451 | 5,766,633 | 6/1998 | Milstein et al. | 424/489 |
| 5,576,009 | 11/1996 | Nastke et al. | 424/408 | 5,770,187 | 6/1998 | Hasebe et al. | 424/69 |
| 5,578,324 | 11/1996 | Dohi et al. | 424/499 | 5,770,222 | 6/1998 | Unger et al. | 424/450 |
| 5,578,325 | 11/1996 | Domb et al. | 424/501 | 5,770,231 | 6/1998 | Mesens et al. | 424/497 |
| 5,578,709 | 11/1996 | Woiszwillo | 5330/410 | 5,770,559 | 6/1998 | Manning et al. | 514/2 |
| 5,594,091 | 1/1997 | Igari et al. | 528/271 | 5,773,032 | 6/1998 | Engel et al. | 424/501 |
| 5,595,760 | 1/1997 | Cherif-Cheikh | 424/464 | 5,776,706 | 7/1998 | Siiman et al. | 435/7 |
| 5,595,762 | 1/1997 | Derrieu et al. | 424/490 | 5,776,885 | 7/1998 | Orsolini et al. | 514/2 |
| 5,597,531 | 1/1997 | Liberti et al. | 423/57 | 5,780,060 | 7/1998 | Levy et al. | 424/489 |
| 5,609,886 | 3/1997 | Wantier et al. | 424/497 | 5,783,214 | 7/1998 | Royer | 424/499 |
| 5,612,027 | 3/1997 | Galin et al. | 424/78 | 5,783,567 | 7/1998 | Hedley et al. | 514/44 |
| 5,618,926 | 4/1997 | Salamone et al. | 530/403 | 5,788,978 | 8/1998 | Passeron et al. | 424/426 |
| 5,620,699 | 4/1997 | Meadows | 424/428 | 5,792,475 | 8/1998 | Davis et al. | 424/489 |
| 5,626,877 | 5/1997 | Amsden et al. | 424/489 | 5,795,719 | 8/1998 | Richard et al. | 435/6 |
| 5,629,294 | 5/1997 | diZerega et al. | 514/18 | 5,801,033 | 9/1998 | Hubbell et al. | 435/182 |
| 5,631,020 | 5/1997 | Okada et al. | 424/451 | 5,804,212 | 9/1998 | Illum | 424/434 |
| 5,631,021 | 5/1997 | Okada et al. | 424/451 | 5,807,757 | 9/1998 | Andrianov et al. | 436/535 |
| 5,635,216 | 6/1997 | Thompson | 424/501 | 5,811,124 | 9/1998 | Fernandez et al. | 424/489 |
| 5,635,405 | 6/1997 | Brouwer | 436/525 | 5,851,451 | 12/1998 | Takechi et al. | 264/4 |
| 5,635,609 | 6/1997 | Levy et al. | 536/2 | 6,090,925 | * 7/2000 | Woiszwillo et al. | 530/410 |
| 5,637,309 | 6/1997 | Tajima et al. | 424/423 | | | | |
| 5,637,568 | 6/1997 | Orsolini et al. | 514/15 | | | | |
| 5,639,468 | 6/1997 | Rodgers et al. | 424/426 | | | | |
| 5,639,480 | 6/1997 | Bodmer et al. | 424/426 | | | | |
| 5,641,515 | 6/1997 | Ramtoola | 424/189 | | | | |
| 5,641,745 | 6/1997 | Ramtoola | 514/11 | | | | |
| 5,643,604 | 7/1997 | Angeles Uribe et al. | 424/489 | | | | |
| 5,643,607 | 7/1997 | Okada et al. | 424/493 | | | | |
| 5,648,095 | 7/1997 | Illum et al. | 424/489 | | | | |
| 5,648,099 | 7/1997 | Batich et al. | 424/497 | | | | |
| 5,650,173 | 7/1997 | Ramstack et al. | 424/489 | | | | |
| 5,652,220 | 7/1997 | Heya et al. | 414/18 | | | | |
| 5,654,006 | 8/1997 | Fernandez et al. | 424/489 | | | | |
| 5,654,008 | 8/1997 | Herbert et al. | 424/489 | | | | |
| 5,654,010 | 8/1997 | Johnson et al. | 424/502 | | | | |
| 5,656,297 | 8/1997 | Bernstein et al. | 424/484 | | | | |
| 5,658,593 | 8/1997 | Orly et al. | 424/499 | | | | |
| 5,662,916 | 9/1997 | Nastke et al. | 424/408 | | | | |
| 5,662,938 | 9/1997 | Vert et al. | 424/501 | | | | |
| 5,665,394 | 9/1997 | Igari et al. | 424/501 | | | | |
| 5,665,428 | 9/1997 | Cha et al. | 427/213 | | | | |
| 5,665,702 | 9/1997 | Shalaby et al. | 514/9 | | | | |
| 5,667,808 | 9/1997 | Johnson et al. | 424/50 | | | | |
| 5,672,659 | 9/1997 | Shalaby et al. | 525/54 | | | | |
| 5,674,521 | 10/1997 | Gehrke et al. | 424/423 | | | | |
| 5,674,531 | 10/1997 | Ahlers et al. | 424/489 | | | | |
| 5,674,534 | 10/1997 | Zale et al. | 424/501 | | | | |
| 5,679,377 | 10/1997 | Bernstein et al. | 424/491 | | | | |
| 5,681,811 | 10/1997 | Ekwuribe | 514/8 | | | | |
| 5,683,723 | 11/1997 | Spenlehauer et al. | 424/501 | | | | |
| 5,686,085 | 11/1997 | Bordier et al. | 424/401 | | | | |
| 5,686,385 | 11/1997 | Akashi et al. | 504/116 | | | | |
| 5,690,954 | 11/1997 | Illum | 424/434 | | | | |
| 5,691,060 | 11/1997 | Levy | 428/402 | | | | |
| 5,700,459 | 12/1997 | Krone et al. | 424/78 | | | | |
| 5,700,486 | 12/1997 | Canal et al. | 424/501 | | | | |
| 5,705,196 | 1/1998 | Soon-Shiong et al. | 428/408 | | | | |
| 5,711,968 | 1/1998 | Tracy et al. | 424/487 | | | | |
| 5,716,640 | 2/1998 | Kamei et al. | 424/451 | | | | |
| 5,716,644 | 2/1998 | Skiba et al. | 424/49 | | | | |
| 5,725,804 | 3/1998 | Yen | 1/1 | | | | |
| 5,725,871 | 3/1998 | Illum | 424/434 | | | | |
| 5,731,005 | 3/1998 | Ottoboni et al. | 424/499 | | | | |
| 5,736,161 | 4/1998 | Garces et al. | 424/493 | | | | |
| 5,744,166 | 4/1998 | Illum | 424/501 | | | | |
| 5,747,060 | 5/1998 | Sackler et al. | 424/426 | | | | |

FOREIGN PATENT DOCUMENTS

| | | |
|---|---|---|
| 00359246A2 | 3/1990 | (EP) . |
| 00381543A1 | 8/1990 | (EP) . |
| 0 429 307 A2 | 11/1990 | (EP) . |
| 0 430 574 A2 | 11/1990 | (EP) . |
| 0 414 223 A2 | 2/1991 | (EP) . |
| 00421577A2 | 4/1991 | (EP) . |
| 0 293 632 B1 | 1/1992 | (EP) . |
| 00465081A1 | 1/1992 | (EP) . |
| 00486959A1 | 5/1992 | (EP) . |
| 00505966A2 | 9/1992 | (EP) . |
| 0 357 401 B1 | 3/1993 | (EP) . |
| 0 535 937 A1 | 4/1993 | (EP) . |
| 0 350 246 B1 | 6/1993 | (EP) . |
| 00545913A1 | 6/1993 | (EP) . |
| 0 580 428 A1 | 1/1994 | (EP) . |
| 00582459A1 | 2/1994 | (EP) . |
| 00585151A1 | 3/1994 | (EP) . |
| 00600775A1 | 6/1994 | (EP) . |
| 00603992A1 | 6/1994 | (EP) . |
| 00628307A2 | 12/1994 | (EP) . |
| 0 752 245 A1 | 1/1997 | (EP) . |
| 0 761 213 A2 | 3/1997 | (EP) . |
| 0 582 459 B1 | 1/1998 | (EP) . |
| 0 815 853 A2 | 1/1998 | (EP) . |
| 0 842 657 A1 | 5/1998 | (EP) . |
| 02600673 | 12/1987 | (FR) . |
| 02645967 | 10/1990 | (FR) . |
| 02667240 | 4/1992 | (FR) . |
| 02691465A1 | 11/1993 | (FR) . |
| 1 354 693 | 5/1974 | (GB) . |
| 2 002 319 | 2/1979 | (GB) . |
| 02017125 | 10/1979 | (GB) . |
| 02040863 | 9/1980 | (GB) . |
| 2 079 937 | 1/1982 | (GB) . |
| 02145992 | 4/1985 | (GB) . |
| 02174097 | 10/1986 | (GB) . |
| 02245831 | 1/1992 | (GB) . |
| 02265311 | 9/1993 | (GB) . |
| 352003890 | 1/1977 | (JP) . |
| 354132479 | 10/1979 | (JP) . |
| 35514405 | 11/1980 | (JP) . |
| 356040608 | 4/1981 | (JP) . |
| 356051411 | 5/1981 | (JP) . |
| 56-4915 | 5/1981 | (JP) . |

| | | | | | | |
|---|---|---|---|---|---|---|
| 356079255 | 6/1981 | (JP) . | | 405004924 | 1/1993 | (JP) . |
| 358058468 | 4/1983 | (JP) . | | 5-4924 | 1/1993 | (JP) . |
| 358067616 | 4/1983 | (JP) . | | 405065221 | 3/1993 | (JP) . |
| 58-58145 | 4/1983 | (JP) . | | 405133929 | 5/1993 | (JP) . |
| 58-58146 | 4/1983 | (JP) . | | 405176974 | 7/1993 | (JP) . |
| 358076092 | 5/1983 | (JP) . | | 405255074 | 10/1993 | (JP) . |
| 358092591 | 6/1983 | (JP) . | | 405292899 | 11/1993 | (JP) . |
| 358224687 | 12/1983 | (JP) . | | 405294826 | 11/1993 | (JP) . |
| 359010512 | 1/1984 | (JP) . | | 405301897 | 11/1993 | (JP) . |
| 359036540 | 2/1984 | (JP) . | | 5-309261 | 11/1993 | (JP) . |
| 59-066-425 | 4/1984 | (JP) . | | 6-49185 | 2/1994 | (JP) . |
| 360028915 | 2/1985 | (JP) . | | 406055059 | 3/1994 | (JP) . |
| 360039564 | 3/1985 | (JP) . | | 6-100436 | 4/1994 | (JP) . |
| 60-100516 | 6/1985 | (JP) . | | 406211648 | 8/1994 | (JP) . |
| 60-214728 | 10/1985 | (JP) . | | 406316524 | 11/1994 | (JP) . |
| 360260641 | 12/1985 | (JP) . | | 6-316524 | 11/1994 | (JP) . |
| 361015733 | 1/1986 | (JP) . | | 7-41428 | 2/1995 | (JP) . |
| 361056076 | 3/1986 | (JP) . | | 407097334 | 4/1995 | (JP) . |
| 361063613 | 4/1986 | (JP) . | | 7/96166 | 4/1995 | (JP) . |
| 361078718 | 4/1986 | (JP) . | | 407275688 | 10/1995 | (JP) . |
| 61-126-016 | 6/1986 | (JP) . | | 407278018 | 10/1995 | (JP) . |
| 361155325 | 7/1986 | (JP) . | | 407316244 | 12/1995 | (JP) . |
| 361218516 | 9/1986 | (JP) . | | 408133990 | 5/1996 | (JP) . |
| 361254244 | 11/1986 | (JP) . | | 408157389 | 6/1996 | (JP) . |
| 362000859 | 1/1987 | (JP) . | | 8-151321 | 6/1996 | (JP) . |
| 362007440 | 1/1987 | (JP) . | | 408225454 | 9/1996 | (JP) . |
| 362059207 | 3/1987 | (JP) . | | 8-225454 | 9/1996 | (JP) . |
| 362105908 | 5/1987 | (JP) . | | 408278307 | 10/1996 | (JP) . |
| 362174009 | 7/1987 | (JP) . | | 8-259460 | 10/1996 | (JP) . |
| 362259587 | 11/1987 | (JP) . | | 408295638 | 11/1996 | (JP) . |
| 362263120 | 11/1987 | (JP) . | | 8-295638 | 11/1996 | (JP) . |
| 3W62262740 | 11/1987 | (JP) . | | 409132524 | 5/1997 | (JP) . |
| 363005019 | 1/1988 | (JP) . | | 409151136 | 6/1997 | (JP) . |
| 363045219 | 2/1988 | (JP) . | | 409221420 | 8/1997 | (JP) . |
| 363091325 | 4/1988 | (JP) . | | 409248137 | 9/1997 | (JP) . |
| 63-077821 | 4/1988 | (JP) . | | 409290146 | 11/1997 | (JP) . |
| 86 223 230 | 4/1988 | (JP) . | | 7205355 | 10/1972 | (NL) . |
| 363115817 | 5/1988 | (JP) . | | WO 08400294A1 | 2/1984 | (WO) . |
| 363141907 | 6/1988 | (JP) . | | WO 8702893A1 | 5/1987 | (WO) . |
| 363174925 | 7/1988 | (JP) . | | WO 08807870A1 | 10/1988 | (WO) . |
| 363207382 | 8/1988 | (JP) . | | WO 009003123A2 | 4/1990 | (WO) . |
| 363252543 | 10/1988 | (JP) . | | WO 09011129A1 | 10/1990 | (WO) . |
| 1018-440 | 1/1989 | (JP) . | | WO 09003123A2 | 11/1990 | (WO) . |
| 401018440 | 1/1989 | (JP) . | | WO 09201443A1 | 2/1992 | (WO) . |
| 401022816 | 1/1989 | (JP) . | | WO 09210282A1 | 6/1992 | (WO) . |
| 401038026 | 2/1989 | (JP) . | | WO 92/10282 | 6/1992 | (WO) . |
| 401043343 | 2/1989 | (JP) . | | WO 92/1184 | 7/1992 | (WO) . |
| 401079111 | 3/1989 | (JP) . | | WO 93/00076 | 1/1993 | (WO) . |
| 1159-047 | 6/1989 | (JP) . | | WO 93/02712 | 2/1993 | (WO) . |
| 401159047 | 6/1989 | (JP) . | | WO 09313755A1 | 7/1993 | (WO) . |
| 401163135 | 6/1989 | (JP) . | | WO 09313809A1 | 7/1993 | (WO) . |
| 401168289 | 7/1989 | (JP) . | | WO 09317784A1 | 7/1993 | (WO) . |
| 401168337 | 7/1989 | (JP) . | | WO/93/13808 | 7/1993 | (WO) . |
| 1-221310 | 9/1989 | (JP) . | | WO/93/14110 | 7/1993 | (WO) . |
| 401281085 | 11/1989 | (JP) . | | WO 09321906A1 | 11/1993 | (WO) . |
| 402001287 | 1/1990 | (JP) . | | WO 09325191A2 | 12/1993 | (WO) . |
| 2-48037 | 2/1990 | (JP) . | | WO 09402106A1 | 2/1994 | (WO) . |
| 402124814 | 5/1990 | (JP) . | | | | |
| 402229545 | 9/1990 | (JP) . | | | | |
| 403030831 | 2/1991 | (JP) . | | | | |
| 403033657 | 2/1991 | (JP) . | | | | |
| 403061493 | 3/1991 | (JP) . | | | | |
| 403191780 | 8/1991 | (JP) . | | | | |
| 403271234 | 12/1991 | (JP) . | | | | |
| 404018015 | 1/1992 | (JP) . | | | | |
| 404018022 | 1/1992 | (JP) . | | | | |
| 404046193 | 2/1992 | (JP) . | | | | |
| 404074117 | 3/1992 | (JP) . | | | | |
| 404074522 | 3/1992 | (JP) . | | | | |
| 404208217 | 7/1992 | (JP) . | | | | |
| 4-313341 | 11/1992 | (JP) . | | | | |

| | | |
|---|---|---|
| WO 09403269A1 | 2/1994 | (WO) . |
| WO 09404261A1 | 3/1994 | (WO) . |
| WO 94/04261 | 3/1994 | (WO) . |
| WO 09408627A1 | 4/1994 | (WO) . |
| WO 09409898A1 | 5/1994 | (WO) . |
| WO/94/20856 | 9/1994 | (WO) . |
| WO 09423767A1 | 10/1994 | (WO) . |
| WO 09427718A1 | 12/1994 | (WO) . |
| WO 09505806A1 | 3/1995 | (WO) . |
| WO 09509613A1 | 4/1995 | (WO) . |
| WO 09511690A1 | 5/1995 | (WO) . |
| WO 09512399A1 | 5/1995 | (WO) . |
| WO 95/13798 | 5/1995 | (WO) . |
| WO 09521018A1 | 8/1995 | (WO) . |
| 9522318A1 | 8/1995 | (WO) . |
| WO/95/24929 | 9/1995 | (WO) . |
| WO/95/26718 | 10/1995 | (WO) . |
| WO 09528838A1 | 11/1995 | (WO) . |
| WO 09531187A1 | 11/1995 | (WO) . |
| WO 09535097A1 | 12/1995 | (WO) . |
| WO 09600295A1 | 1/1996 | (WO) . |
| WO 09600537A1 | 1/1996 | (WO) . |
| WO 09601048A1 | 1/1996 | (WO) . |
| WO 09603142A1 | 2/1996 | (WO) . |
| WO 09610992A1 | 4/1996 | (WO) . |
| WO 09611671A1 | 4/1996 | (WO) . |
| WO 98/07410 | 2/1998 | (WO) . |

OTHER PUBLICATIONS

Waldmann, T. A., "Monolclonal Antibodies in Diagnosis and Therapy", Science,252, pp. 1657–1662, (1991).

Abbott, Nicholas and Hatton, T. A. "Liquid–Liquid Extraction for Protein Separations" Aug. 1988).

Sheu, M. et al., "Entrapment of Bioactive Compounds Within Native Albumin Beads: II. Effects of Rate and Extent oc Crosslinking on Microbead Properties," Journal of Parental Science & Technology, vol. 40, No. 6, pp. 259–265 (Nov.–Dec. 1986).

Chen, Y., Burton, M. A. Codde, J. P., Napoli, S., Martins, I. J. and Gray, B. N., "Evaluation of Ion–exchange Microspheres as Carriers for the Anticancer Drug Doxorubicin: In–vitro Studies", J. Pharm. Pharmacol. 44, pp. 211–215, (1992).

Rubino, O. P., Kowalsky, R. and Swarbrick, J., "Albumin Microspheres as a Drug Delivery System: Relation Among Turbidity Ratio, Degree of Cross–linking, and Drug Release", Pharmaceutical Research, vol. 10, No. 7, pp. 1059–1065 (1993).

Williams, C. A. and Chase, M. W. (eds.), "Methods in Immunology and Immunochemistry", Adademic Press, New York, pp. 288–289 (1968).

Gupta, P. K. and Hung, C. T., "Albumin microspheres I: physico–chemical characteristics ", J. Microencapsulation, vol. 6, No. 4, pp. 427–462, (1989).

Ralston, G. B., "Effects of 'Crowding' in Protein Solutions", Journal of Chemical Education, vol. 67, No. 10, pp. 857–860, (Oct. 1990).

Mahadevan, H. and Hall, C. K., "Theory of Precipitation of Protein Mixtures by Nonionic Polymer", AIChE Journal, vol. 38, No. 4, (Apr. 1992).

Lee, T. K., Sokoloski, T. D., and Royer, G. P., "Serum Albumin Beads: An Injectable, Biodegradable System for the Sustained Release of Drugs", Science, vol. 213, pp. 233–235, (Jul. 1981).

Carrell, S. "Novel Systems for Drug Delivering Biotechnology Drugs Explored", Genetic Engineering News, pp. 2 and 10, (Feb. 1993).

Madhusudhan, R., et al., "Modification of Enzyme Activity in Reversed Micelles Through Clathrate Hydrate Formation", Biotechnol, Prog., vol. 6, pp. 465–471, (1990).

Phillips, J. B., et al., "Protein Recovery from Reversed Micellar Solutions through Contact with a Pressurized Gas Phase", Biotechnol, Prog., vol. 7, pp. 43–48, (1991).

Guttman, H. J., Anderson, C.F., and Record, Jr., M.T. "Analyses of Thermodynamic Data for Concentrated Hemoglobin Solutions Using Scaled Particle Theory: Implications for a Simple Two–State Model of Water in Thermodynamic Analyses of Crowding in Vitro and In Vivo", vol. 68, pp. 835–846, (Mar. 1995).

Sheu, Ming–Thau and Sokoloski, Theodore, D., "Entrapment of Bioactive Compounds Within Native Albumin Beads: III. Evaluation of Parameters Affecting Drug Release" Journal of Parenternal Science & Technology, No. 6/Nov.–Dec. 1986, pp. 259–265.

* cited by examiner

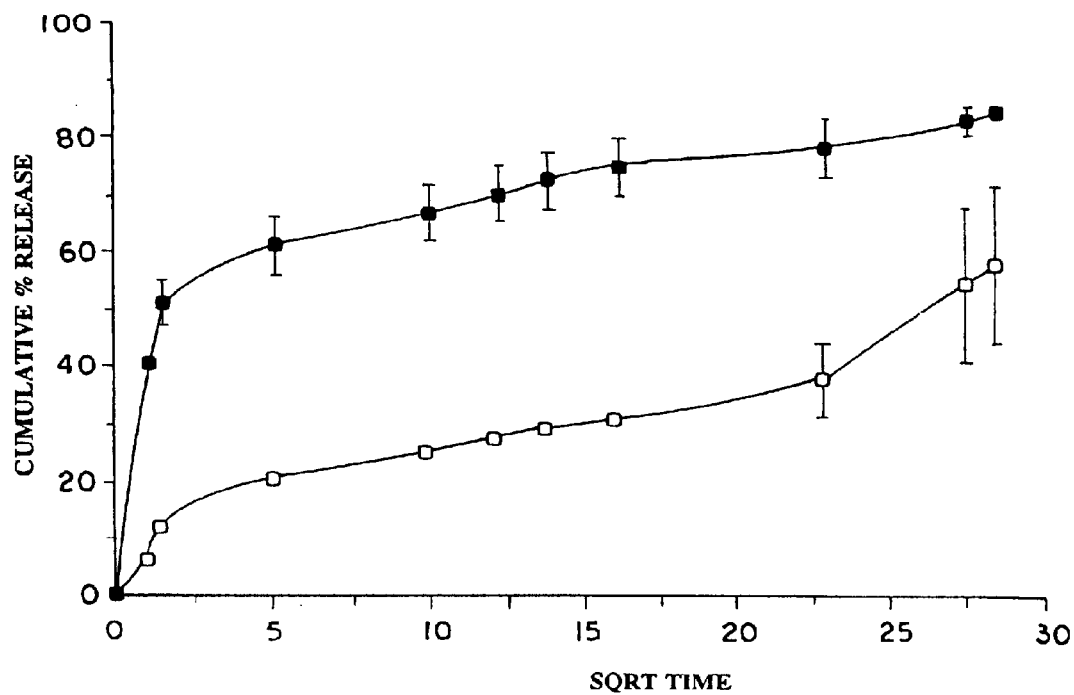
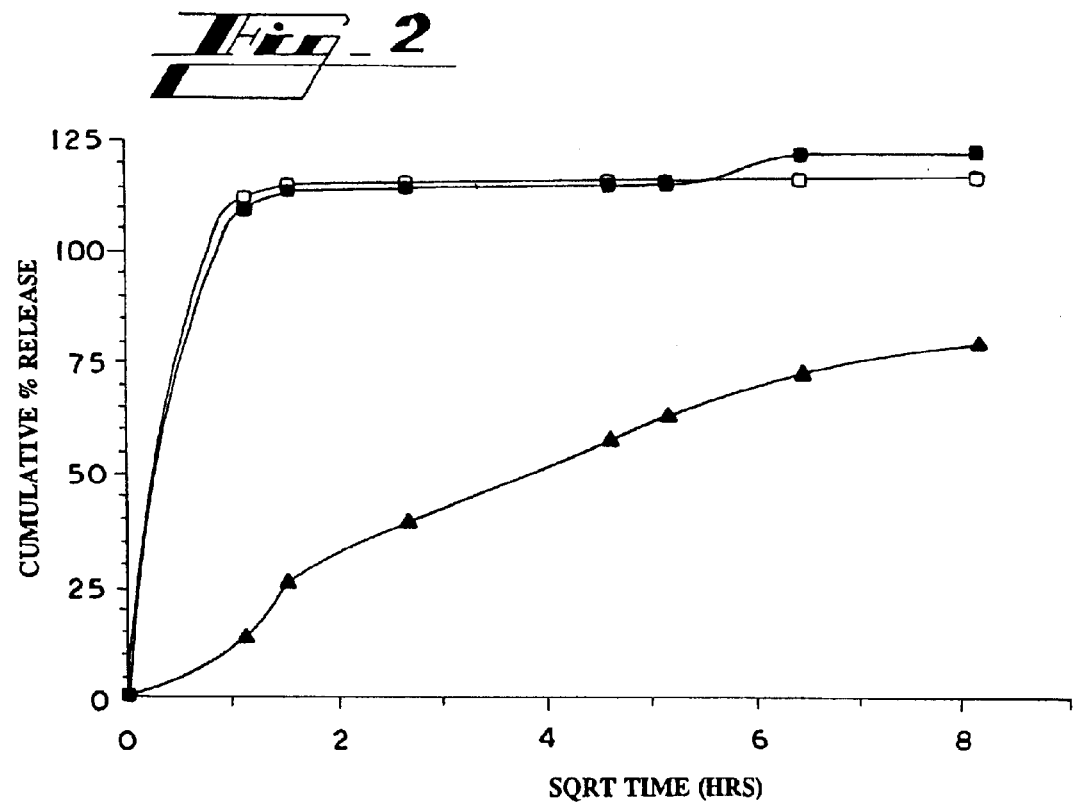

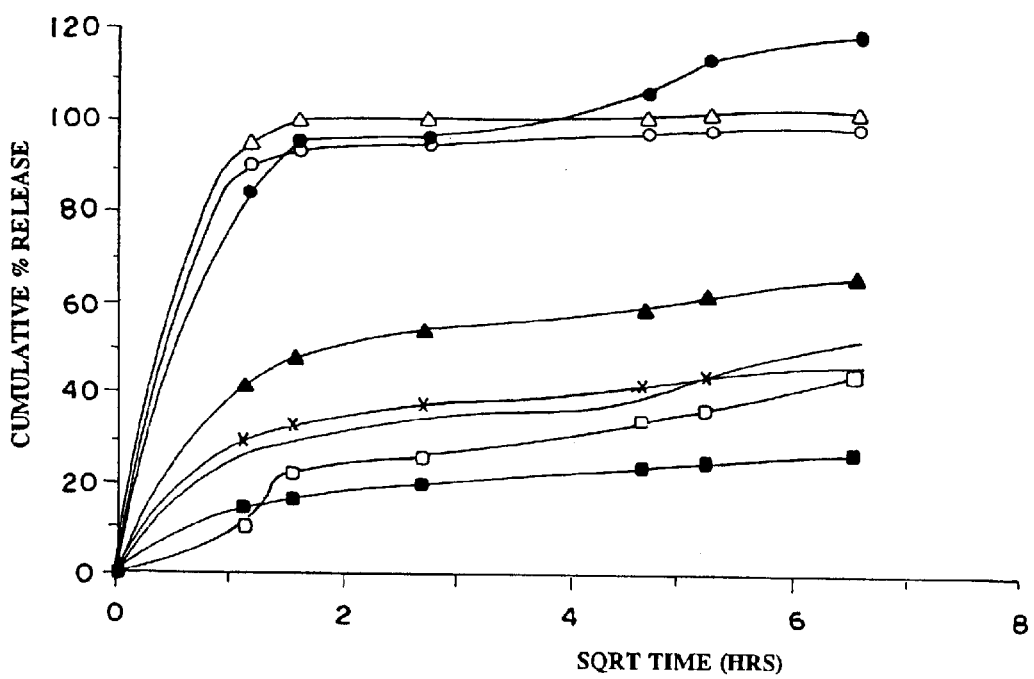
Fig_5
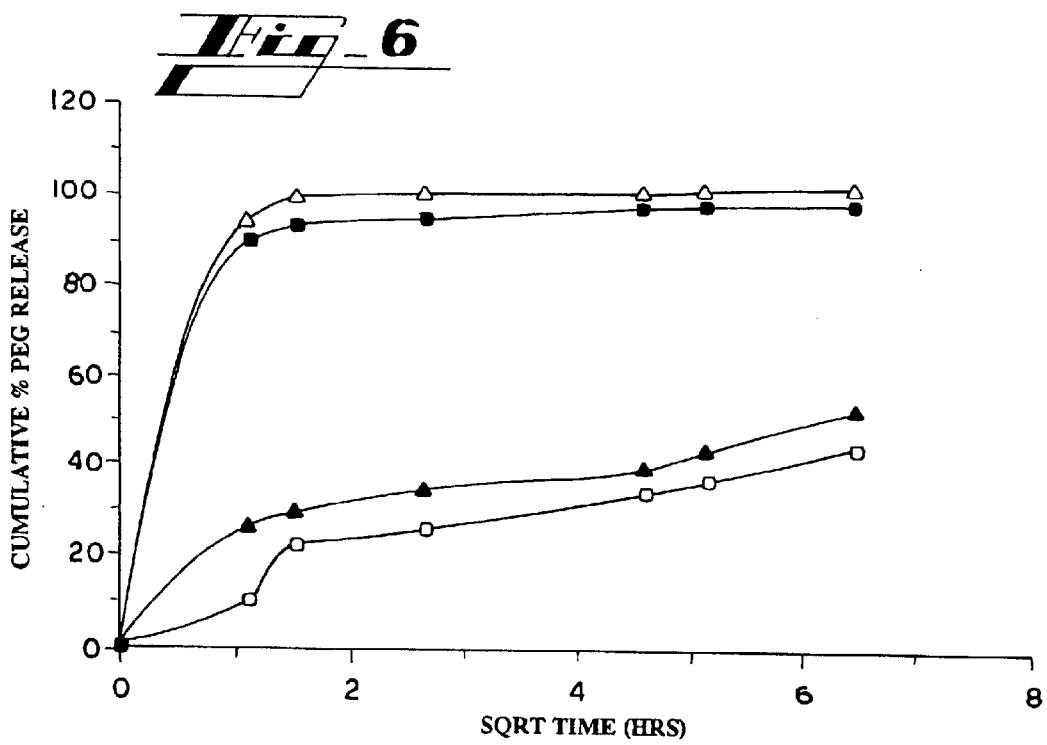
Fig_6

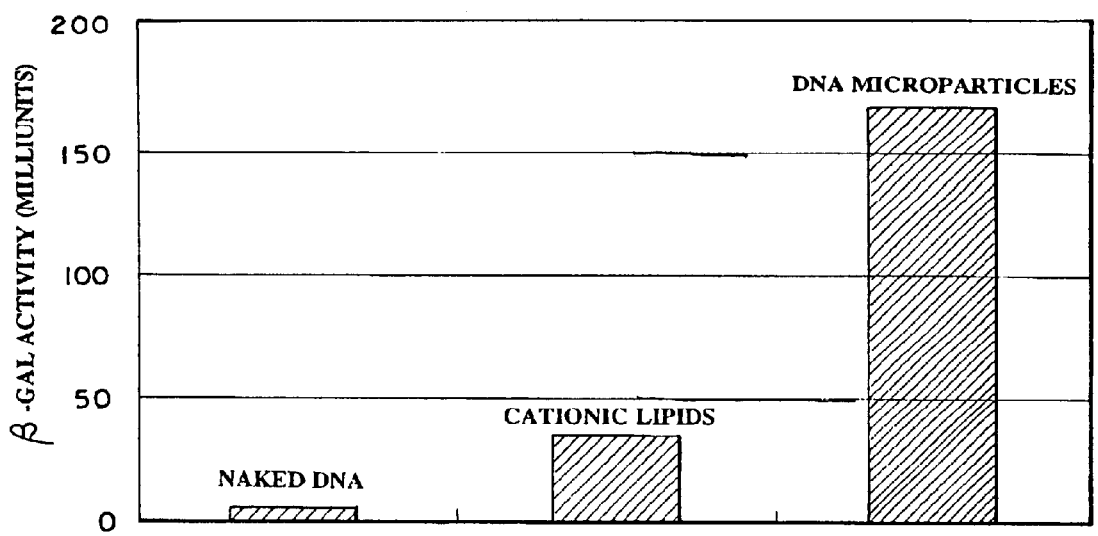
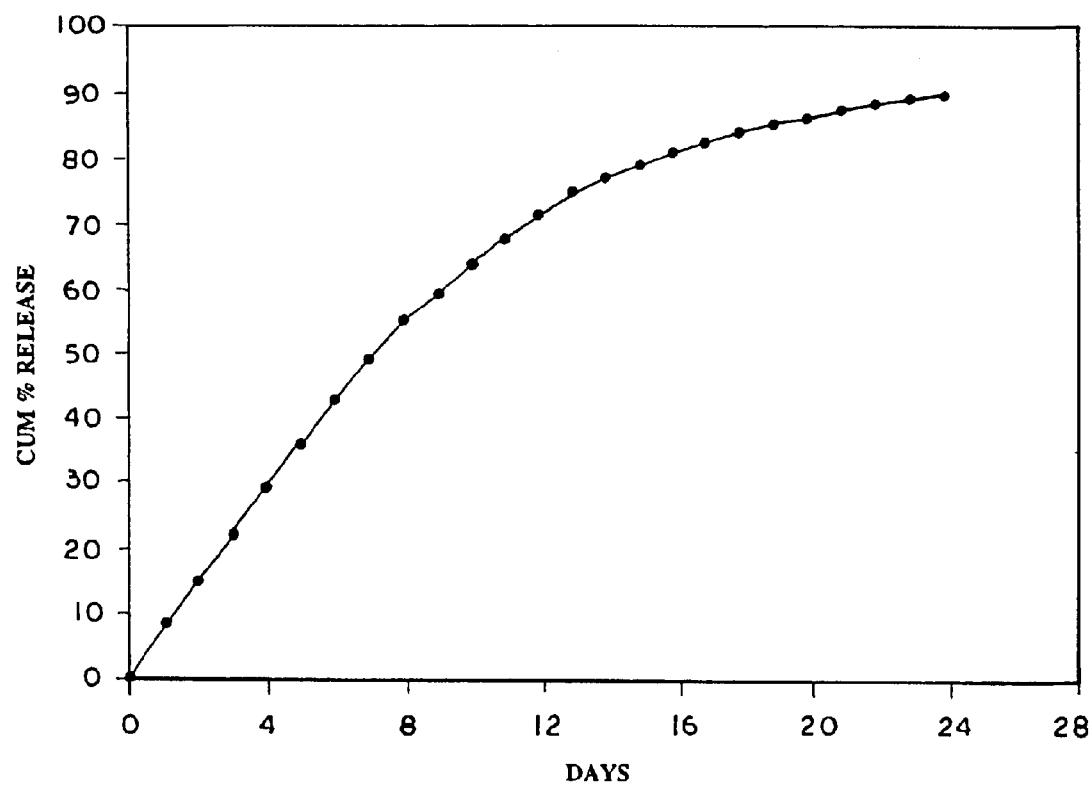

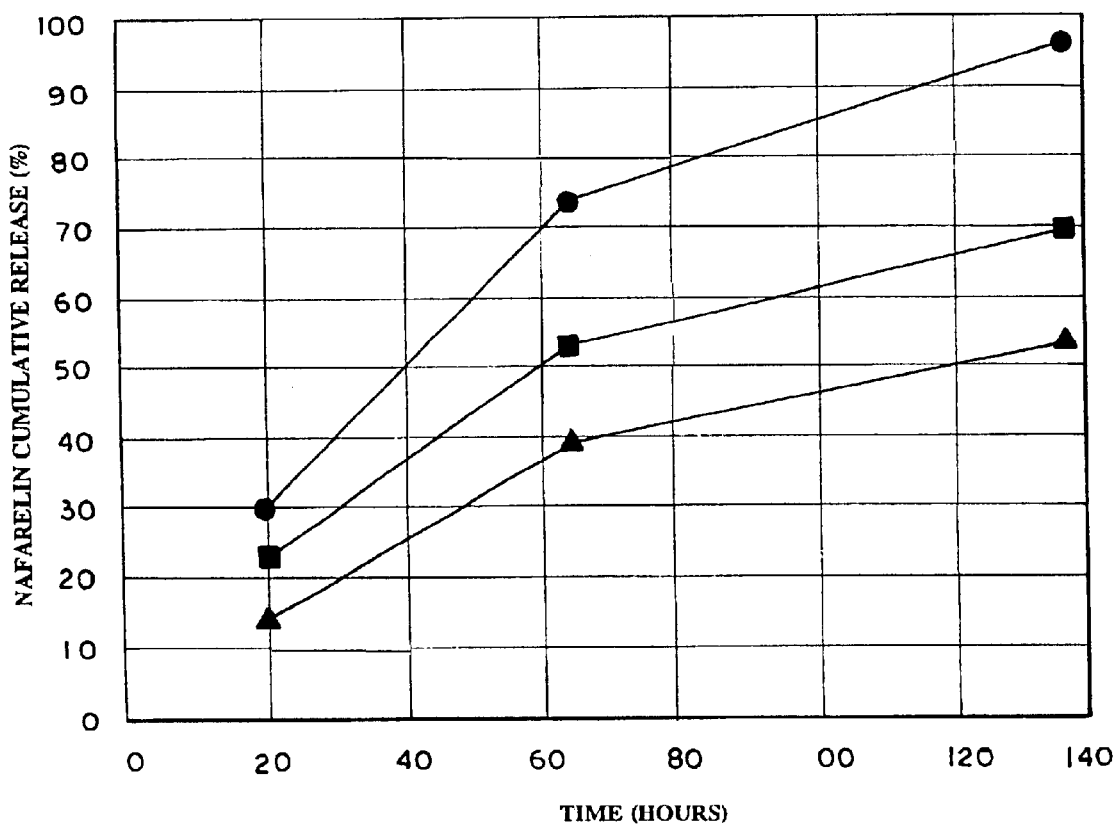
Fig_9

MACROMOLECULAR MICROPARTICLES AND METHODS OF PRODUCTION AND USE

This application is a continuation of application Ser. No. 08/699,586, filed Aug. 19, 1996, entitled Macromolecular Micropartides and Methods of Production and Use, and now U.S. Pat. No. 6,090,925, which is a continuation-in-part of application Ser. No. 08/206,456, filed Mar. 4, 1994, U.S. Pat. No. 5,578,709, which is a continuation-in-part of application Ser. No. 08/028,237, filed Mar. 9, 1993, abandoned, the entire contents of which documents are incorporated herein by reference.

BACKGROUND OF THE INVENTION

Microparticles, microspheres, and microcapsules, referred to herein collectively as "microparticles", are solid or semi-solid particles having a diameter of less than one millimeter, more preferably less than 100 microns, which can be formed of a variety of materials, including synthetic polymers, proteins, and polysaccharides. Microparticles have been used in many different applications, primarily separations, diagnostics, and drug delivery.

The most well known examples of microparticles used in separations techniques are those which are formed of polymers of either synthetic or protein origin, such as polyacrylamide, hydroxyapatite or agarose. These polymeric microparticles are commonly used to separate molecules such as proteins based on molecular weight and/or ionic charge or by interaction with molecules chemically coupled to the microparticles.

In the diagnostic area, microparticles are frequently used to immobilize an enzyme, substrate for an enzyme, or labelled antibody, which is then interacted with a molecule to be detected, either directly or indirectly.

In the controlled drug delivery area, molecules are encapsulated within microparticles or incorporated into a monolithic matrix, for subsequent release. A number of different techniques are routinely used to make these microparticles from synthetic polymers, natural polymers, proteins and polysaccharides, including phase separation, solvent evaporation, emulsification, and spray drying. Generally the polymers form the supporting structure of these microspheres, and the drug of interest is incorporated into the polymer structure. Exemplary polymers used for the formation of microspheres include homopolymers and copolymers of lactic acid and glycolic acid (PLGA) as described in U.S. Pat. No. 5,213,812 to Ruiz, U.S. Pat. No. 5,417,986 to Reid et al., U.S. Pat. No. 4,530,840 to Tice et al., U.S. Pat. No. 4,897,268 to Tice et al., U.S. Pat. No. 5,075,109 to Tice et al., U.S. Pat. No. 5,102,872 to Singh et al., 5,384,133 to Boyes et al., 5,360,610 to Tice et al., and European Patent Application Publication Number 248,531 to Southern Research Institute; block copolymers such as tetronic 908 and poloxamer 407 as described in U.S. Pat. No. 4,904,479 to Illum; and polyphosphazenes as described in U.S. Pat. No. 5,149,543 to Cohen et al. Microspheres produced using polymers such as these exhibit a poor loading efficiency and are often only able to incorporated a small percentage of the drug of interest into the polymer structure. Therefore, substantial quantities of microspheres often must be administered to achieve a therapeutic effect.

Spherical beads or particles have been commercially available as a tool for biochemists for many years. For example, antibodies conjugated to beads create relatively large particles specific for particular ligands. The large antibody-coated particles are routinely used to crosslink receptors on the surface of a cell for cellular activation, are bound to a solid phase for immunoaffinity purification, and may be used to deliver a therapeutic agent that is slowly released over time, using tissue or tumor-specific antibodies conjugated to the particles to target the agent to the desired site.

The most common method of covalently binding an antibody to a solid phase matrix is to derivatize a bead with a chemical conjugation agent and then bind the antibody to the activated bead. The use of a synthetic polymeric bead rather than a protein molecule allows the use of much harsher derivatization conditions than many proteins can sustain, is relatively inexpensive, and often yields a linkage that is stable to a wide range of denaturing conditions. A number of derivatized beads are commercially available, all with various constituents and sizes. Beads formed from synthetic polymers such as polyacrylamide, polyacrylate, polystyrene, or latex are commercially available from numerous sources such as Bio-Rad Laboratories (Richmond, Calif.) and LKB Produkter (Stockholm, Sweden). Beads formed from natural macromolecules and particles such as agarose, crosslinked agarose, globulin, deoxyribose nucleic acid, and liposomes are commercially available from sources such as Bio-Rad Laboratories, Pharmacia (Piscataway, N.J.), and IBF (France). Beads formed from copolymers of polyacrylamide and agarose are commercially available from sources such as IBF and Pharmacia. Magnetic beads are commercially available from sources such as Dynal Inc. (Great Neck, N.Y.).

The disadvantages of the microparticles or beads currently available are that they are difficult and expensive to produce. Microparticles produced by these known methods have a wide particle size distribution, often lack uniformity, and fail to exhibit long term release kinetics when the concentration of active ingredients is high. Furthermore, the polymers used in these known methods are dissolved in organic solvents in order to form microspheres. The microspheres must therefore be produced in special facilities designed to handle organic solvents. These organic solvents could denature proteins or peptides contained in the microparticles. Residual organic solvents could be toxic when administered to humans or animals.

In addition, the available microparticles are rarely of a size sufficiently small to fit through the aperture of the size of needle commonly used to administer therapeutics or to be useful for administration by inhalation. For example, microparticles prepared using polylactic glycolic acid (PLGA) are large and have a tendency to aggregate. A size selection step, resulting in product loss, is necessary to remove particles too large for injection. PLGA particles that are of a suitable size for injection must be administered through a large bore needle to accommodate the large particle size, often causing discomfort for the patient.

Generally all currently available microspheres are activated to release their contents in aqueous media and therefore must be lyophilized to prevent premature release. In addition, particles such as those prepared using the PLGA system exhibit release kinetics based on both erosion and diffusion. In this type of system, an initial burst or rapid release of drug is observed. This burst effect can result in unwanted side effects in patients to whom the particles have been administered.

Microparticles prepared using lipids to encapsulate target drugs are currently available. For example, lipids arranged in bilayer membranes surrounding multiple aqueous compartments to form particles may be used to encapsulate water soluble drugs for subsequent delivery as described in U.S. Pat. No. 5,422,120 to Sinil Kim. These particles are generally greater than 10 μm in size and are designed for intraarticular, intrathecal, subcutaneous and epidural administration. Alternatively, liposomes have been used for intravenous delivery of small molecules. Liposomes are spherical particles composed of a single or multiple phospholipid and cholesterol bilayers. Liposomes are 30 μm or greater in size and may carry a variety of water-soluble or lipid-soluble drugs. Liposome technology has been hindered by problems including purity of lipid components, possible toxicity, vesicle heterogeneity and stability, excessive uptake and manufacturing or shelf-life difficulties.

Therefore, there is an on-going need for development of new methods for making microparticles, particularly those that can be adapted for use in the separations, diagnostic and drug delivery area.

SUMMARY OF THE INVENTION

Microparticles, methods of production, and methods of use thereof are provided. In accordance with the method, macromolecules are mixed with a soluble polymer or mixture of soluble polymers, such as linear or branched polymers at a pH near the isoelectric point of the macromolecule in the presence of an energy source such as heat for a predetermined length of time.

The microparticles are composed of polymer and macromolecules. At least 40% and less than 100% of the final weight of each microparticle is composed of macromolecules. Preferably, the concentration of polymer is less than 30% by weight of the total microparticle weight.

The microparticles can be made to exhibit short-term or long-term release kinetics, thereby providing either rapid or sustained release of macromolecules.

The microparticles are composed of a matrix of substantially homogeneously distributed, intertwined macromolecules and polymers. The microparticle allows aqueous fluids to enter and solubilized macromolecules and polymers to exit the microparticle.

The microparticle preparation method is mild and does not adversely affect the biological activity of the macromolecules present therein. Therefore, if desired, the macromolecules released from the microparticles retain their natural bioactivity.

The polymer is one capable of removing water from the macromolecules to cause volume exclusion. Suitable polymers include soluble linear or branched polymers, preferably those having a high molecular weight. Soluble polymers are defined herein as polymers that are soluble in a water miscible solvent or aqueous solution. Therefore, the polymers are water soluble, semi-water soluble, or water insoluble. Types of polymers that may be used include carbohydrate-based polymers, polyaliphatic alcohols, poly (vinyl) polymers, polyacrylic acids, polyorganic acids, polyamino acids, co-polymers and block co-polymers, tertpolymers polyethers, naturally occurring polymers, polyimids, surfactants, polyesters, branched and cyclopolymers, and polyaldehydes. Most preferably, the polymer is dextran or a polymer mixture of polyvinylpyrrolidone and polyethylene glycol.

The macromolecules are those having a tertiary and quaternary structure or capable of having a tertiary and quaternary structure, and include, but are not limited to, proteins, peptides, carbohydrates, polysaccharides, polysaccharide-protein conjugates, nucleic acids, viruses, virus particles, conjugates or complexes of small molecules and proteins, or mixtures thereof. Organic or inorganic synthetic pharmaceutical drugs may also be incorporated into the microparticles.

The microparticles have a generally uniform size and shape. The characteristics of the microparticles may be altered during preparation by manipulating the polymer concentration, reaction temperature, pH, macromolecule concentration, or the length of time the macromolecule is exposed to the energy source.

The microparticles are useful for a wide variety of separations, diagnostic, therapeutic, industrial, commercial, cosmetic, and research purposes or for any purpose requiring the incorporation of and stabilization of an active molecule, reactant or drug.

It is therefore an object of the present invention to provide a process for making microparticles that is relatively simple, rapid, and inexpensive.

It is a further object of the present invention to provide a process for making microparticles that uses only aqueous or aqueous miscible solvents and does not utilize a water-in-oil emulsion in the manufacturing of the microparticles.

It is a further object of the present invention to provide a process for making microparticles in which the macromolecule concentration is at least 40% by weight.

It is a further object of the present invention to provide a process for making microparticles that permits manipulation of the microparticle release kinetics.

It is a further object of the present invention to provide a process for making microparticles of a uniform size for injection into a patient without particle size selection.

It is a further object of the present invention to provide microparticles that exhibit sustained release of macromolecule.

It is a further object of the present invention to provide microparticles that can release macromolecules which have retained their biological activity.

It is a further object of the present invention to provide microparticles for use in medical and diagnostic applications, such as drug delivery, vaccination, gene therapy and histopathological or in vivo tissue or tumor imaging.

It is a further object of the present invention to provide microparticles suitable for oral or parenteral administration; mucosal administration; ophthalmic administration; intravenous, subcutaneous, intraarticular, or intramuscular injection; administration by inhalation; and topical administration.

These and other objects of the present invention will become apparent after reading the following detailed description of the disclosed embodiments and the appended claims.

BRIEF DESCRIPTION OF THE DRAWINGS

FIG. 1 is a graph showing the cumulative percent of radiolabelled polyethylene glycol (PEG) and radiolabelled bovine serum albumin (BSA) released from microparticles versus the square root of time in hours. The black square symbol represents PEG, and the open square symbol represents BSA.

FIG. 2 is a graph showing the cumulative percent of radiolabelled bovine serum albumin (BSA) released from microparticles prepared with three different concentrations of polymer versus the square root of time in hours. The gray square symbol represents a total polymer concentration of 50%, the open square symbol represents a total polymer concentration of 40%, and the black triangle symbol represents a total polymer concentration of 25%.

FIG. 5 is a graph showing the cumulative percent of radiolabelled polyethylene glycol (PEG) released from microparticles prepared with three different concentrations of polymer at various incubation temperatures versus the square root of time in hours. The symbols are the same as those described in FIG. 4.

FIG. 6 is a graph showing the cumulative percent of radiolabelled polyethylene glycol (PEG) released from microparticles prepared with three different concentrations of polymer at an incubation temperature including 58° C. versus the square root of time in hours. The open triangle symbol represents a total polymer concentration of 50% and incubation at 58° C., the black square symbol represents a total polymer concentration of 40% and incubation at 58° C., the gray triangle symbol represents a total polymer concentration of 25% and incubation at 37° C. and 58° C., and the open square symbol represents a total polymer concentration of 25% and incubation at 58° C.

FIG. 7 is a bar graph showing the amount of expressed gene product by β-Galactosidase activity in milliunits versus microparticle formation for naked DNA, cationic liposomes containing DNA, and DNA microparticles.

FIG. 8 is a graph of cumulative percent release of leuprolide acetate release from microparticles over time in days.

FIG. 9 is a graph of cumulative percent nafarelin acetate release versus time in hours for three concentrations of zinc sulfate used during microparticle preparation. The circle symbol represents 0.01 M zinc sulfate; the square symbol represents 0.1 M zinc sulfate; and the triangle symbol represents 1 M zinc sulfate.

DETAILED DESCRIPTION OF THE DISCLOSED EMBODIMENTS

Figure 3:
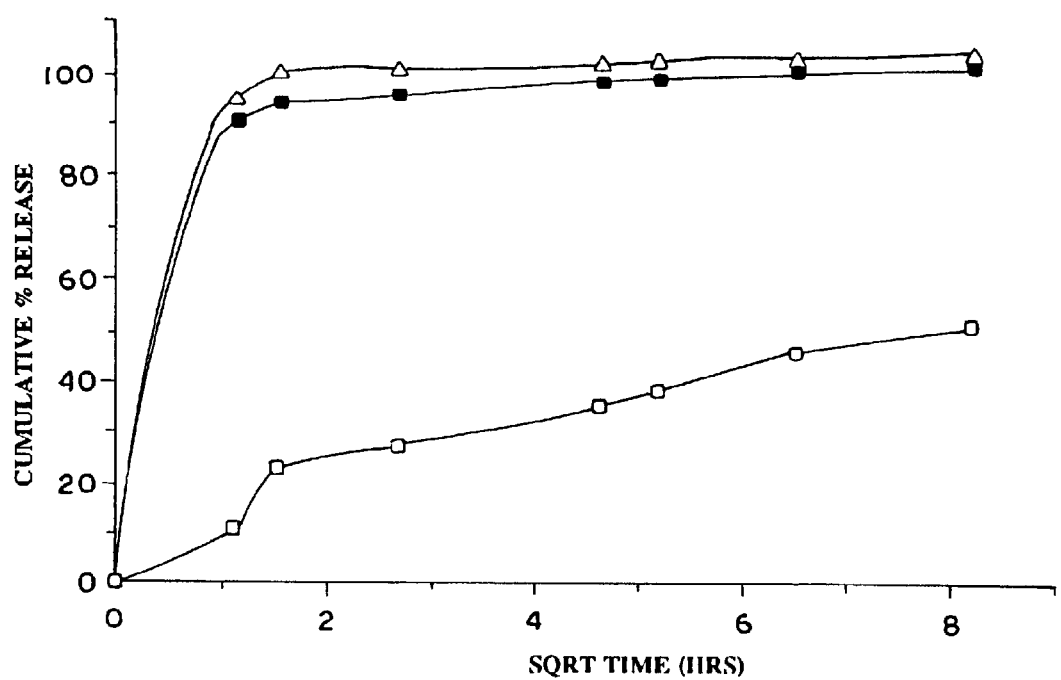
FIG. 3 is a graph showing the cumulative percent of radiolabelled polyethylene glycol (PEG) released from microparticles prepared with three different concentrations of polymer versus the square root of time in hours. The open triangle symbol represents a total polymer concentration of 50%, the black square symbol represents a total polymer concentration of 40%, and the open square symbol represents a total polymer concentration of 25%.

Microparticle, methods of production, and methods of use thereof are provided. The microparticles are prepared by mixing or dissolving macromolecules with a soluble polymer or mixture of soluble polymers, such as linear or branched polymers, at a pH near the isoelectric point of the macromolecule. The macromolecule and polymer mixture is exposed to an energy source, such as heat, for a predetermined length of time to form microparticles. The microparticles are then separated from the unincorporated reagents by separation methods such as filtration or centrifugation.

The macromolecule or combination of macromolecules compose at least 40% and less than 100% by weight of the final weight of each microparticle. Preferably, the polymer concentration in the microparticle is greater than 0% and less than or equal to 30% by weight. The types of macromolecules forming the microparticles include, but are not limited to, proteins, peptides, carbohydrates, conjugates, nucleic acids, viruses, or mixtures thereof.

Each microparticle is composed of macromolecules and polymer molecules, which are intertwined or interspersed in the microparticle and are generally homogeneously distributed. The inner matrix is water soluble, and, when solubilized, the inner matrix diffuses through the outer surface under appropriate conditions as explained in more detail below. The microparticles exhibit a narrow size distribution and have a generally uniform shape. Size distribution is also adjustable by modifying the conditions and reagents used during the preparation process and may be associated with release kinetics as described below. The microparticles are generally less than 10 μm in diameter. The uniform shape of the microparticles is substantially spherical, which is why the microparticles are also referred to herein as "microspheres".

The outer surface of each microparticle is permeable to water and dissolved macromolecules and not only allows aqueous fluids to enter the microparticle, but also allows solubilized macromolecule and polymer to exit the microparticle. The microparticles can be made to release macromolecule and polymer from the interior of the microparticle when placed in an appropriate aqueous medium, such as body fluids or a physiologically acceptable buffer under physiological conditions over a prolonged period of time, thereby providing sustained release of macromolecules. In addition, the microparticles can be made to release macromolecule without an initial burst or rapid release of macromolecule. Sustained release is defined herein as release of macromolecules over an extended period of time. The amount of time over which the macromolecules continue to be released from the microparticle depends on the characteristics of the macromolecule being released and the parameters used to form the microparticles, but in all cases is longer than that of free aqueous diffusion of the macromolecule. Microparticles containing pharmaceutical compounds can be made to release the pharmaceutical compound with the macromolecule and polymer as described above.

As discussed briefly above and in more detail below, the characteristics of the microparticles may be manipulated during preparation by adjusting the type of polymer, polymer concentration, polymer composition, incubation temperature, pH, macromolecule concentration, or the length of time the macromolecule is exposed to the energy source.

The microparticles may be administered to a human or animal by oral or parenteral administration, including intravenous, subcutaneous or intramuscular injection; administration by inhalation; intraarticular administration; mucosal administration; ophthalmic administration; and topical administration. Intravenous administration includes catheterization or angioplasty. Administration may be for purposes such as therapeutic and diagnostic purposes as discussed below.

Formation of Microparticles

Microparticles are produced by mixing macromolecules in solution or a liquid phase with a polymer or mixture of polymers in solution or a liquid phase in the presence of an energy source for a sufficient amount of time to form particles. The solution is preferably an aqueous solution. Either the macromolecule solution is added to the polymer or the polymer solution is added to the macromolecule solution to cause removal of water from, or dehydration of, the macromolecules. This process is also referred to by those skilled in the art as volume exclusion.

The pH of the macromolecule-polymer solution is adjusted, either before, after or during the mixing of the polymer with the macromolecule, to a pH near the isoelectric point (pI) of the macromolecule, preferably within 3 to 4 pH units of the pI of the macromolecule, most preferably within 1.5 to 2 pH units of the pI of the macromolecule.

The pH adjustment may be made by adding an acid, base, either in solution or solid form, or a buffer or other pH-adjusting solution or salt, to either the macromolecule solution, the polymer solution, or to the mixture of macromolecule and polymer in accordance with methods well known to those skilled in the art. Preferably the polymer is dissolved in a buffer having a pH near the pI of the macromolecule, and then the pH-adjusted polymer solution is added to the macromolecule, which has been dissolved in an aqueous solution. The pH of the final solution should remain near the pI of the macromolecule.

The macromolecule and polymer solution is then exposed to an energy source, such as heat, radiation, or ionization, alone or in combination with sonication, vortexing, mixing or stirring, for a predetermined length of time to form microparticles. The resulting microparticles are then separated from any unincorporated components present in the solution by physical separation methods well known to those skilled in the art and may then be washed.

The length of incubation time is dependent upon the respective concentrations of polymer and macromolecule and the level of energy of the energy source. Microparticle formation can begin to occur immediately upon exposure to the energy source. Preferably, the macromolecule and polymer mixture is heated at a temperature greater than room temperature for between approximately 5 minutes and 24 hours. Most preferably, the polymer and macromolecules are mixed, by stirring or rocking, for 30 minutes at a temperature between approximately 37° C. and 70° C.

Macromolecule

The macromolecule forming the microparticle is any molecule having a tertiary and quaternary structure or capable of having a tertiary and quaternary structure. Most preferably, the macromolecule is a biomolecule such as a protein, including enzymes and recombinant proteins, a peptide, polypeptide, carbohydrate, polysaccharide, carbohydrate- or polysaccharide-protein conjugate, nucleic acid, virus, virus particle, conjugate of a small molecule (such as a hapten) and protein, or mixtures thereof. An organic or inorganic natural or synthetic pharmaceutical compound or drug may be incorporated into the microparticles by attaching the drug to a macromolecule, such as a protein, and then forming the microparticles from the macromolecule-drug complex or conjugate. It will be understood by those skilled in the art that a compound incapable of having a tertiary and quaternary structure can be formed into a microparticle by incorporation or coupling of the compound into a carrier molecule that has a tertiary and quaternary structure. It will be further understood by those skilled in the art that the macromolecule can be a portion of a molecule such as, for example, a peptide, a single-stranded segment of a double-stranded nucleic acid molecule, or a virus particle, having a tertiary and quaternary structure. It will also be understood that the term "macromolecule" includes a plurality of macromolecules and includes combinations of different macromolecules such as a combination of a pharmaceutical compound and an affinity molecule for targeting the pharmaceutical compound to a tissue, organ or tumor requiring treatment. It will be further understood that an affinity molecule can be either the receptor portion or the ligand portion of a receptor-ligand interaction. Examples of ligands that interact with other biomolecules include viruses, bacteria, polysaccharides, or toxins that act as antigens to generate an immune response when administered to an animal and cause the production of antibodies.

Suitable compounds or macromolecules include, but are not limited to, betaxolol™, diclofenac™, doxorubicin, rifampin™, leuprolide acetate, luteinizing hormone releasing hormone (LHRH), (D-Tryp6)-LHRH, nafarelin acetate, insulin, sodium insulin, zinc insulin, protamine, lysozyme, alpha-lactalbumin, basic fibroblast growth factor (bFGF), beta-lactoglobulin, trypsin, carbonic anhydrase, ovalbumin, bovine serum albumin (BSA), human serum albumin (HSA), phosphorylase b, alkaline phosphatase, β-galactosidase, IgG, fibrinogen, poly-L-lysine, IgM, DNA, desmopressin acetate™, growth hormone releasing factor (GHRF), somatostatin, antide, Factor VIII, G-CSF/GM-CSF, human growth hormone (hGH), beta interferon, anti-thrombin III, alpha interferon, alpha interferon 2b.

The incubation conditions are typically optimized to incorporate approximately 100% of the macromolecule in the reaction mixture by adjusting the pH, temperature, concentration of macromolecule, or length of reaction or incubation. In general, less energy is required to form microparticles at higher concentrations of macromolecule.

Microparticles composed of nucleic acids are preferably prepared by first mixing the nucleic acid either with a protein, such as bovine serum albumin, or, because nucleic acids are anions, the addition of a cation, such as polylysine, which aids greatly in the formation of microparticles.

As mentioned above, a small molecule or compound incapable of having a tertiary and quaternary structure, such as a peptide or pharmaceutical compound, can be formed into a microparticle by incorporation or coupling of the compound into a carrier molecule that has a tertiary and quaternary structure. This may be achieved in several ways. For example, microparticles may be formed as described herein using a macromolecule having a tertiary and quaternary structure, such as a protein, and then the small molecule or compound is bound inside and or on the surface of the microparticle. Alternatively, the small molecule or compound is bound to the macromolecule having a tertiary and quaternary structure using hydrophobic or ionic interactions and then microparticles are formed from the macromolecule-small molecule complex using the method described herein. A third way to make microparticles from small molecules is to prepare microparticles using a macromolecule having a tertiary and quaternary structure in such a way that the microparticle has a net charge and then add a small molecule or compound having an opposite net charge so that the small molecule is physically attracted to and remains attached to the microparticle, but can be released over time under the appropriate conditions.

Alternatively, different types of non-covalent interactions such as hydrophobic or affinity interactions may be used to allow attachment and subsequent release of small molecules.

When preparing microparticles containing protein, a protein stabilizer such as glycerol, fatty acids, sugars such as sucrose, ions such as zinc, sodium chloride, or any other protein stabilizers known to those skilled in the art may be added prior to the addition of the polymers during microparticle formation to minimize protein denaturation.

Labelled Macromolecule

Prior to being incorporated into a microparticle, the macromolecule may be labelled with a detectable label. The various types of labels and methods of labelling proteins and nucleic acid molecules are well known to those skilled in the art. It will be understood by those skilled in the art that a magnetic substance, such as a metal, is included within the definition of the term label. For example, the macromolecule can be labelled with a metallic substance, such as a metal, so that the microparticles can be separated from other substances in a solution with the aid of a magnetic device.

Several other specific labels or reporter groups are set forth below. For example, the label can be a radiolabel such as, but not restricted to, $^{32}P$, $^{3}H$, $^{14}C$, $^{35}S$, $^{125}I$, or $^{131}I$. A $^{32}P$ label can be conjugated to a protein with a conjugating reagent or incorporated into the sequence of a nucleic acid molecule by nick-translation, end-labelling or incorporation of labelled nucleotide. For example, a $^{3}H$, $^{14}C$ or $^{35}S$ label can be incorporated into a nucleotide sequence by incorporation of a labelled precursor or by chemical modification, whereas an $^{125}I$ or $^{131}I$ label is generally incorporated into a nucleotide sequence by chemical modification. Detection of a label can be by methods such as scintillation counting, gamma ray spectrometry or autoradiography.

The label can also be a Mass or Nuclear Magnetic Resonance (NMR) label such as, for example, $^{13}C$, $^{15}N$, or $^{19}O$. Detection of such a label can be by Mass Spectrometry or NMR.

Dyes, chemiluminescent agents, bioluminescent agents and fluorogens can also be used to label the macromolecule. Examples of dyes useful for labelling nucleic acids include ethidium bromide, acridine, propidium and other intercalating dyes, and 4', 6'-diamidino-2-phenylindole (DAPI) (Sigma Chemical Company, St. Louis, Mo.) or other nucleic acid stains. Examples of fluorogens include fluorescein and derivatives, phycoerythrin, allo-phycocyanin, phycocyanin, rhodamine, Texas Red or other fluorogens. The fluorogens are generally attached by chemical modification. The dye labels can be detected by a spectrophotometer and the fluorogens can be detected by a fluorescence detector.

The macromolecule can also be labelled with a chromogen (enzyme substrate) to provide an enzyme or affinity label, or enzyme. Alternatively, the macromolecule can be biotinylated so that it can be utilized in a biotin-avidin reaction, which may also be coupled to a label such as an enzyme or fluorogen. The macromolecule can be labelled with peroxidase, alkaline phosphatase or other enzymes giving a chromogenic or fluorogenic reaction upon addition of substrate.

A label can also be made by incorporating any modified base, amino acid, or precursor containing any label, incorporation of a modified base or amino acid containing a chemical group recognizable by specific antibodies, or by detecting any bound antibody complex by various means including immunofluorescence or immuno-enzymatic reactions. Such labels can be detected using enzyme-linked immunoassays (ELISA) or by detecting a color change with the aid of a spectrophotometer.

Coated Microparticles

Molecules, distinct from the macromolecules of which the microparticles are composed, may be attached to the outer surface of the microparticles by methods known to those skilled in the art to "coat" or "decorate" the microparticles. The ability to attach molecules to the outer surface of the microparticle is due to the high concentration of macromolecule in the microparticle. These molecules are attached for purposes such as to facilitate targeting, enhance receptor mediation, and provide escape from endocytosis or destruction. For example, biomolecules such as phospholipids may be attached to the surface of the microparticle to prevent endocytosis by endosomes; receptors, antibodies or hormones may be attached to the surface to promote or facilitate targeting of the microparticle to the desired organ, tissue or cells of the body; and polysaccharides, such as glucans, may be attached to the outer surface of the microparticle to enhance or to avoid uptake by macrophages.

In addition, one or more cleavable molecules may be attached to the outer surface of or within the microparticles. The cleavable molecules are designed so that the microparticles are first targeted to a predetermined site under appropriate biological conditions and then, upon exposure to a change in the biological conditions, such as a pH change, the molecules are cleaved causing release of the microparticle from the target site. In this way, microparticles are attached to or taken up by cells due to the presence of the molecules attached to the surface of the microparticles. When the molecule is cleaved, the microparticles remain in the desired location, such as within the cytoplasm or nucleus of a cell, and are free to release the macromolecules of which the microparticles are composed. This is particularly useful for drug delivery, wherein the microparticles contain a drug that is targeted to a specific site requiring treatment, and the drug can be slowly released at that site. The preferred site of cleavage is a diester bond.

The microparticles may also be coated with one or more stabilizing substances, which may be particularly useful for long term depoting with parenteral administration or for oral delivery by allowing passage of the microparticles through the stomach or gut without dissolution. For example, microparticles intended for oral delivery may be stabilized with a coating of a substance such as mucin, a secretion containing mucopolysaccharides produced by the goblet cells of the intestine, the submaxillary glands, and other mucous glandular cells.

Additionally, the particles can be non-covalently coated with compounds such as fatty acids or lipids. The coating may be applied to the microparticles by immersion in the solubilized coating substance, spraying the microparticles with the substance or other methods well known to those skilled in the art.

Polymer

The polymer or mixture of polymers used to prepare the microparticles and contained within the microparticles is one that is capable of removing water from or dehydrating the macromolecule or capable of causing volume exclusion. Suitable polymers include soluble linear or branched polymers, preferably those having a high molecular weight. Soluble polymers are defined herein as polymers that are soluble in a water miscible solvent or aqueous solution. Therefore, the polymers are water soluble, semi-water soluble, or water insoluble. Preferably, the polymers are water soluble or soluble in a water miscible solvent. Polymers may be solubilized by first being dissolved in an organic solvent and then combining the polymer solution with an aqueous solvent. Suitable polymers include the following categories of polymers: 1) carbohydrate-based polymers, such as methylcellulose, carboxymethyl cellulose-based polymers, dextran, polydextrose, chitins, chitosan, and starch (including hetastarch), and derivatives thereof; 2) polyaliphatic alcohols such as polyethylene oxide and derivatives thereof including polyethylene glycol (PEG), PEG-acrylates, polyethyleneimine, polyvinyl acetate, and derivatives thereof; 3) poly(vinyl) polymers such as poly(vinyl) alcohol, poly(vinyl)pyrrolidone, poly (vinyl)phosphate, poly(vinyl)phosphonic acid, and derivatives thereof; 4) polyacrylic acids and derivatives thereof; 5) polyorganic acids, such as polymaleic acid, and derivatives thereof; 6) polyamino acids, such as polylysine, and polyimino acids, such as polyimino tyrosine, and derivatives thereof; 7) co-polymers and block co-polymers, such as poloxamer 407 or Pluronic L-101™ polymer, and derivatives thereof; 8) tert-polymers and derivatives thereof; 9) polyethers, such as poly(tetramethylene ether glycol), and derivatives thereof; 10) naturally occurring polymers, such as zein, chitosan and pullulan, and derivatives thereof; 11) polyimids, such as poly n-tris(hydroxymethyl) methylmethacrylate, and derivatives thereof; 12) surfactants, such as polyoxyethylene sorbitan, and derivatives thereof; 13) polyesters such as poly(ethylene glycol) (n)monomethyl ether mono(succinimidyl succinate)ester, and derivatives thereof; 14) branched and cyclo-polymers, such as branched PEG and cyclodextrins, and derivatives thereof; and 15) polyaldehydes, such as poly (perfluoropropylene oxide-b-perfluoroformaldehyde), and derivatives thereof.

The preferred polymer is polyvinylpyrrolidone, polyethylene glycol, dextran, polyoxyethylene-polyoxypropylene copolymer, polyvinyl alcohol, or mixtures thereof, the characteristics of which are described in more detail below. The polymer or polymer mixture may be prepared in accordance with the methods set forth in U.S. Pat. No. 5,525,519 to James E. Woiszwillo, or PCT Patent Application No. US93-00073 (International Publication No. WO 93/14110), filed Jan. 7, 1993 and published on Jul. 22, 1993 by James E. Woiszwillo, both of which are incorporated herein by reference, in which the polymer is dissolved in water or an aqueous solution, such as a buffer, in a concentration between approximately 1 and 50 g/100 ml depending on the molecular weight of the polymer. The preferred total polymer concentration in the polymer solution is between 10% and 80%, expressed as weight/volume percent. The preferred concentration of each polymer in the polymer solution is between 5% and 50% As discussed above, the pH of the polymer solution may be adjusted before being combined with the macromolecule so that the addition of the polymer causes a pH adjustment of the macromolecule solution, most preferably within one pH unit of the pI. The pH may be adjusted during the preparation of the polymer solution by preparing the polymer in a buffer having a predetermined pH. Alternatively, the pH may be adjusted after preparation of the polymer solution with an acid or a base.

Polyoxyethylene-polyoxypropylene copolymer, also known as poloxamer, is sold by BASF (Parsippany, N.J.) and is available in a variety of forms with different relative percentages of polyoxyethylene and polyoxypropylene within the copolymer.

PVP is a non-ionogenic, hydrophilic polymer having a mean molecular weight ranging from approximately 10,000 to 700,000 and the chemical formula $(C_6H_9NO)_n$. PVP is also known as poly[(1-(2-oxo-1-pyrrolidinyl)ethylene], Povidone™, Polyvidone™, RP 143™, Kollidon™, Peregal ST™, Periston™, Plasdone™, Plasmosan™, Protagent™, Subtosan™, and Vinisil™. PVP is non-toxic, highly hygroscopic and readily dissolves in water or organic solvents.

Polyethylene glycol (PEG), also known as poly (oxyethylene) glycol, is a condensation polymer of ethylene oxide and water having the general chemical formula $HO(CH_2CH_2O)_nH$.

Dextran is a term applied to polysaccharides produced by bacteria growing on a sucrose substrate. Native dextrans produced by bacteria such as *Leuconostoc mesenteroides* and *Lactobacteria dextranicum* usually have a high molecular weight. Dextrans are routinely available and are used in injectable form as plasma expanders in humans.

Polyvinyl alcohol (PVA) is a polymer prepared from polyvinyl acetates by replacement of the acetate groups with hydroxyl groups and has the formula $(CH_2CHOH)_n$. Most polyvinyl alcohols are soluble in water.

PEG, dextran, PVA and PVP are commercially available from chemical suppliers such as the Sigma Chemical Company (St. Louis, Mo.).

Most preferably, the polymer is a polymer mixture containing an aqueous solution of PVP having a molecular weight between 10,000 and 360,000, most preferably 40,000, and PEG having a molecular weight between 200 and 35,000. PVP having a molecular weight of 40,000 and PEG having a molecular weight of 3500 is preferred. Preferably, the PVP is dissolved in an acetate buffer and PEG is added to the aqueous PVP solution. The concentration of each polymer is preferably between 1 and 40 g/100 ml depending of the molecular weight of each polymer. Equal concentrations of PVP and PEG generally provide the most favorable polymer mixture for the formation of microparticles.

An alternative preferred polymer is a dextran, having a molecular weight from approximately 3000 to 500,000 daltons.

The volume of polymer added to the macromolecule varies depending on the size, quantity and concentration of the macromolecule. Preferably, two volumes of the polymer mixture at a 5–50% total polymer concentration are added to one volume of a solution containing the macromolecule. The polymer is present in a liquid phase during the reaction with macromolecule.

Energy Source

Microparticles are formed by incubation of the macromolecule-polymer solution in the presence of an energy source for a predetermined length of time. The preferred energy source is heat. However, it will be understood by those skilled in the art that other energy sources include heat, radiation, and ionization, alone or in combination with sonication, vortexing, mixing or stirring. Microparticle formation can occur immediately upon exposure to the energy source or may require an extended exposure to the energy source depending on the characteristics of the components and conditions. Preferably, the macromolecule-polymer solution mixture, is incubated in a water bath at a temperature greater than or equal to 37° C. and less than or equal to 90° C. for between approximately 5 minutes and 2 hours. Most preferably, the mixture is incubated for 5–30 minutes at a temperature between 50° C. and 90° C. It should be noted that microparticles may be formed at lower temperatures by utilizing a higher macromolecule concentration. The maximum incubation temperature is determined by the characteristics of the macromolecule and the ultimate function of the microparticle. For example, for a microparticle in which the macromolecule is a protein, a temperature less than approximately 70° C. is preferred to retain protein activity.

Purification of Microparticles

The formed microparticles are separated from the non-incorporated components of the incubation mixture by conventional separation methods well known to those skilled in the art. Preferably, the incubation mixture is centrifuged so that the microparticles sediment to the bottom of the centrifuge tube and the non-incorporated components remain in the supernatant, which is then removed by decanting. Alternatively, a suspension containing formed microparticles is filtered so that the microparticles are retained on the filter and the non-incorporated components pass through the filter.

Further purification of the microparticles is achieved by washing in an appropriate volume of a washing solution. The preferred washing solution is a buffer, most preferably a nonionic aqueous solution or a nonionic aqueous solution containing water soluble polymers. Repeated washings can be utilized as necessary and the microparticles separated from the wash solution as described above.

Microparticle Characteristics

As mentioned above, the characteristics of the microparticles can be altered by manipulating the incubation conditions. For example, the release kinetics of the microparticles may be retarded by increasing the reaction temperature or extending the length of reaction time during microparticle formation. Release kinetics are also manipulated by choosing different polymers, different concentrations of polymers, or different ratios of polymers used in the formation of the microparticles.

Microparticle size, shape and release kinetics can also be controlled by adjusting the microparticle formation conditions. For example, particle formation conditions can be optimized to produce smaller or larger particles or the overall incubation time or incubation temperature can be increased, resulting in particles which have prolonged release kinetics.

Microparticle Utility

The microparticles are useful for a wide variety of separations, diagnostic, therapeutic, industrial, commercial, cosmetic, and research purposes as discussed in more detail below. For example, for in vivo diagnostic purposes, the microparticles can include a macromolecule such as an immunoglobulin or cell receptor labelled with a detectable label. Administration of the labelled microparticle to a patient creates an imaging agent for the diagnosis of a proliferative disorder such as cancer or a tool for the evaluation of the success of a therapeutic agent in reducing the proliferation of a particular adverse cell or organism.

For in vitro diagnosis, microparticles containing a macromolecule, such as an immunoglobulin, cell receptor or oligonucleotide probe specific for the cell or organism under investigation, are combined with a test sample, the microparticles are separated from any non-bound components of the sample, and bound molecules are detected by conventional methods.

The microparticles are useful as therapeutic agents and may enable the use of alternative routes of administration when the microparticles include a therapeutic drug and are administered to a patient for slow release or targeted delivery of the drug to the site requiring therapy. The microparticles are also useful as therapeutic or prophylactic agents when the microparticles include a macromolecule that is itself a therapeutic or prophylactic agents such as an enzyme or immunoglobulin. The slow release of such therapeutic agents is particularly useful for therapeutic proteins or peptides having short half-lives that must be administered by injection.

The microparticles are also useful for the purification of molecules from a complex mixture, as a reagent for the detection or quantification of a specific molecule, or for the production of molecules, such as antibodies. For example, microparticles containing a macromolecule, such as an immunoglobulin, can be attached to a chromatography column and used in immunoaffinity chromatography to separate a ligand from a complex mixture.

Alternatively, microparticles including a labelled macromolecule or a mixture of labelled macromolecules specific for different cells or biomolecules, such as cell receptors, can be used to detect changes in the number of cells or biomolecules in response to a particular test condition using techniques such as flow cytometry.

Furthermore, the microparticles can be used as adjuvants for vaccine production wherein antigen-containing microparticles are injected into a research animal, such as a mouse or rabbit, to trigger an enhanced immune response for the production of antibodies to the antigen.

Additional commercial uses include cleaning formulations, such as the formation of enzyme particles for addition to detergents; cosmetics, such as the formation of collagen particles to be suspended in a lotion or cream; ink; and paint.

In Vitro Diagnostics

In vitro assays

The microparticles described herein are useful as solid phase particles in an assay, such as an enzyme-linked immunosorbant assay, dot-blot, or Western blot, for the detection of a particular target such as a cell, biomolecule or drug in a biological sample. The microparticles designed for this use are composed of affinity molecules specific for the target molecule. For example, the macromolecule is an immunoglobulin, cell receptor or oligonucleotide probe and is bound to a test tube or microtiter plate.

For detection or quantitation of a target molecule of interest, a sample is combined with a solution containing the microparticles, the macromolecules on the microparticles are reacted with the target molecule, the microparticles are separated from any non-bound components of the sample, and microparticles containing bound molecules are detected by conventional methods. Fluorescently stained microparticles are particularly well suited for flow cytometry analysis in accordance with methods well known to those skilled in the art.

Histopathology

The microparticles described herein are useful as visual probes or markers of pathology in a histological sample. The macromolecules of microparticles designed for this use are specific for biomolecules expressed during a particular pathologic condition and are labelled with a detectable label. For example, the macromolecule is an immunoglobulin, cell receptor or oligonucleotide probe specific for an abnormal cell, such as a rapidly proliferating cell, or pathological organism, for example, a virus.

For detection of a pathogenic condition, a histological sample is combined with a solution containing the microparticles, the labelled macromolecules on the microparticles are reacted with the target molecule of interest, and bound microparticles are detected by detecting the label in accordance with methods well known to those skilled in the art.

In Vivo Diagnostics—Imaging

The microparticles described herein are useful as imaging agents for in vivo localization of a particular molecule, cell type or pathologic condition in a manner similar to that described above with regard to the use of the microparticles for histopathology. The macromolecules on microparticles designed for this use are specific for molecules expressed by a particular cell or pathologic organism and are labelled with a detectable label. For example, the macromolecule is an immunoglobulin, cell receptor or oligonucleotide probe specific for a tumor cell or pathological organism, such as a virus.

The microparticles are used to either detect a pathologic condition or to monitor the success of therapy, such as chemotherapy or surgery to ensure that the size of an abnormal tissue tumor has decreased or has been completely excised. For this use, a patient receives an administration of a microparticle solution, preferably intravenously, the labelled macromolecules on the microparticles are given a sufficient amount of time to localize to the affected organ or region of the body, the macromolecule is reacted with a target molecule expressed by the cell or organism under investigation, and bound microparticles are detected by detecting the label by conventional imaging techniques well known to those skilled in the art, such as x-ray.

Drug Delivery Systems

The microparticles are useful for therapy or a prophylaxis when the macromolecule is a therapeutic agent or a pharmaceutical compound that is delivered to a patient and slowly released from the microparticles over time. These microparticles are particularly useful for slow release of drugs with short biological half-lives, such as proteins or peptides. If the pharmaceutical compound cannot be formed into a particle, then it is complexed to a carrier, such as albumin, and the carrier-pharmaceutical compound complex is formed into a microparticle. The microparticle can either provide for the slow release of the agent throughout the body or the microparticle can include an affinity molecule specific for a target tissue, or tumor, and be injected into a patient for targeted slow release of the therapeutic agent, such as an antitumor, antiviral, antibacterial, antiparasitic, or antiarthritic agent, cytokine, hormone, or insulin directly to the site requiring therapy. As discussed above, the affinity molecule may be cleavable.

Microparticles composed of antigenic proteins or polysaccharide-protein conjugates capable of provoking an immune response are particularly suitable for use as vaccines.

The microparticles are also useful as vehicles for gene therapy or the production of "genetic vaccines" when composed of nucleic acids, such as DNA or RNA, that are either incorporated into the DNA of the patient or are transfected into a target cell to produce a desired protein. For example, polynucleotides encoding core proteins of viruses such as influenza or human immunodeficiency virus HIV can be delivered as microparticles for expression of an antigenic protein. This is advantageous in that new vaccines need not be developed as often because viral core proteins mutate to a much lesser extent than the cell surface antigens currently used in vaccines. The nucleic acid microparticles are delivered to mammalian cells in much the same way as naked DNA is delivered. The desired nucleic acid sequence is inserted into a vector, such as plasmid DNA, with a promoter, such as the SV40 promoter or the cytomegalovirus promoter, and optionally may include a reporter gene, such as beta-galactosidase. The nucleic acid is preferably combined with a carrier protein and/or a cation, such as polylysine, to facilitate particle formation as described above. The microparticles are then administered directly to the patient or are transfected into mammalian cells that are then administered to the patient requiring therapy or prophylaxis. The nucleic acid microparticles may include a substance such as chloroquine, which allows nucleic acids to escape from cytoplasmic compartments into the cytoplasm so that it can be more easily transcribed and translated by the cells. Additionally, the microparticles may be coated with a substance that increases the efficiency of translation or may be coated with a substance to provide cell-specific targeting of the microparticles.

Research Applications

The microparticles are useful as research tools for the purification of a biomolecule from a complex mixture, as a reagent for the detection or quantification of a biomolecule, or for the production of biomolecules, such as antibodies.

For example, microparticles composed of a macromolecule, such as an immunoglobulin, are attached to a chromatography column and used in immunoaffinity chromatography to separate a ligand from a complex mixture. It will be understood by those skilled in the art that microparticle for use in high pressure liquid chromatography should be first attached to a non-compressible solid phase sphere or bead so that the column packing maintains its rigid structure under pressure.

Alternatively, microparticles including a labelled macromolecule or a mixture of labelled macromolecules specific for different cells or cell receptors are used to detect changes in the number of cells or cell surface receptors in response to a particular test condition using techniques such as flow cytometry.

The microparticles and methods described above will be further understood with reference to the following non-limiting examples.

EXAMPLE 1

Preparation of Microparticles

Containing a Pharmaceutical Agent

Human serum albumin (HSA) microparticles suitable for use as a drug delivery vehicle were prepared.

Preparation of Rifampicin™-HSA Microparticles

Carbonyl diimidazole (124 mg, Sigma Chemical Co., St. Louis, Mo.) was added to a solution of 50 mg of the antibiotic Rifampicin™ (3-[4-methylpiperazinyl-iminomethyl]rifamycin, Sigma Chemical Co., St. Louis, Mo.) in 2 ml dimethylformamide (DMF). The resulting mixture was allowed to stand at room temperature for four hours. To the mixture was added a mixture of 1 ml of human serum albumin (HSA, 25%, Armour Pharmaceutical Co., Collegeville, Pa.) and 2 ml deionized water. The mixture was left at room temperature overnight. 14 ml of a polymer solution containing 25% PVP (40,000 daltons) and 25% PEG (3,350 daltons) in 0.1 M NaOAc, pH 4 was added to the mixture. The mixture was incubated for 30 minutes at room temperature, for 30 minutes at 37° C., and for 30 minutes at 58° C. and then cooled to room temperature. Particles were isolated by centrifugation, washed with deionized water three times and resuspended in 20 ml of water. The percentage of HSA incorporated into the particles was 74% (assayed by the BCA™ protein assay (Pierce, Rockford, Ill.)). The percentage of Rifampicin™ incorporated into the particles was greater than 6.8%. The average size of the particles was determined to be 68 nm in diameter using a Coulter™ cell sorter.

Preparation of Virazole™-HSA Microparticles

Carbonyl diimidazole (100 mg, Sigma Chemical Co., St. Louis, Mo.) was added to a solution of 36 mg of the antiviral drug Virazole® (ICN Pharmaceuticals, Inc., Costa Mesa, Calif.) in 0.2 ml of dimethylformamide (DMF). The resulting mixture was allowed to stand at room temperature for four hours. To the mixture was added a mixture of 0.2 ml of human serum albumin (HSA) (25%, Armour Pharmaceutical Co., Collegeville, Pa.) and 0.4 ml of deionized water. The mixture was incubated for 30 minutes at room temperature, for 30 minutes at 37° C., and for 30 minutes at 58° C. and then cooled to room temperature. Particles were isolated by centrifugation, washed with deionized water three times and resuspended in 20 ml of water. The percentage of HSA incorporated into the particles was 61% (assayed by the BCA™ protein assay (Pierce, Rockford, Ill.)). The percentage of Virazole® incorporated into the particles was 10%.

EXAMPLE 2

Attachment of Polysaccharide to

Outer Surface of Protein Microparticles

The polysaccharide PRP-AH was coupled to the outer surface of two different protein microparticles.

An adipic acid dihydrazide derivative (AH) of the polyribosylribitol phosphate (PRP) of *Haemophilus influenzae* type b (Hib), one of the major causative organisms of bacterial meningitis, referred to as PRP-AH, was prepared by coupling PRP to adipic acid (Sigma Chemical Co., St. Louis, Mo.) in the presence of cyanogen bromide (Sigma Chemical Co., St. Louis, Mo.) (The PRP was obtained from the Massachusetts Public Health Biologic Laboratory (Jamaica Plain, Mass.)).

Coupling of PRP-AH to Ovalbumin Microparticles

Ovalbumin microparticles were prepared by adding ovalbumin (1%, Sigma Chemical Co., St. Louis, Mo.) to a polymer solution containing 25% PVP (40,000 daltons) and 25% PEG (3,500 daltons). The mixture was incubated for 30 minutes at room temperature, 30 minutes at 37° C., and 30 minutes at 58° C., causing the formation of microparticles. The particles were collected by centrifugation. The average diameter of the particles was determined to be approximately 0.068 μm.

The ovalbumin particles (1.5 mg) in 1 M MES buffer, pH 5.0 (0.1 ml) were combined with the PRP-AH (1.5 mg). Subsequently, 2.79 mg of 1-ethyl-3-(3-dimethylaminopropyl-carbodiimide hydrochloride (EDC, Sigma Chemical Company, St. Louis, Mo.) were added. The reaction was mixed at room temperature for three hours. The particles were collected by centrifugation and washed three times with 1 M MES buffer pH 5.0 (400 μl). The yield of PRP was determined to be 25% by the Anthrone free polysaccharide assay described in METHODS IN IMMUNOLOGY AND IMMUNOCHEMISTRY, Vol. II, Williams, C. A. and Chase, M. W. (eds.), 1968, pp. 288–289, Academic Press, NY. Protein content was determined to be 55% by the BCA™ protein assay (Pierce, Rockford, Ill.). The ratio of PRP to protein was 0.46. The average diameter of the resulting particles was 0.067 μm.

The recovery of free polysaccharide and the loading of polysaccharide on the particles (polysaccharide:ovalbumin ratio) was dependent on the starting ratio of polysaccharide to ovalbumin particle. As the ratio of polysaccharide to ovalbumin particle was increased, the recovery of free polysaccharide was decreased and the loading of polysaccharide onto the particles was increased as shown in Table 1 below.

TABLE 1

Polysaccharide Recovery and Loading on Ovalbumin Microparticles

| Starting Ratio of Polysaccharide: Particle | Polysaccharide Recovery (%) | Loading of Polysaccharide |
|---|---|---|
| 1:1 | 25 | 0.46 |
| 1:2 | 30 | 0.29 |
| 1:4 | 66 | 0.21 |
| 1:8 | 94 | 0.14 |

Coupling of PRP-AH to Tetanus Toxoid Microparticles

Tetanus toxoid, (27 mg/ml, obtained from the Massachusetts Public Health Biologic Laboratory (Jamaica Plain, Mass.)) was combined with two volumes of a polymer solution containing 25% PVP (40,000 daltons) and 25% PEG (3,500 daltons), pH 5.0. The mixture was incubated for 30 minutes at room temperature, 30 minutes at 37° C., and 30 minutes at 58° C., causing the formation of microparticles. The particles were collected by centrifugation. The average diameter of the particles was determined to be approximately 0.082 μm.

The tetanus toxoid particles (0.825 mg) in 1 M MES buffer, pH 5.0 (0.1 ml) were combined with the PRP-AH (1.5 mg). Subsequently, 2.79 mg of 1-ethyl-3-(3-dimethylaminopropyl-carbodiimide hydrochloride (EDC, Sigma Chemical Company, St. Louis, Mo.) were added. The reaction was mixed at room temperature for three hours. The particles were collected by centrifugation and washed three times with 1 M MES buffer pH 5.0 (400 μl). The yield of PRP was determined to be 16% by the Anthrone free polysaccharide assay described in METHODS IN IMMUNOLOGY AND IMMUNOCHEMISTRY, Vol. II, Williams, C. A. and Chase, M. W. (eds.), 1968, pp. 288–289, Academic Press, NY. Protein content was determined to be 99% by the BCA™ protein assay (Pierce, Rockford, Ill.). The ratio of PRP to protein was 0.1. The average diameter of the resulting particles was 0.080 μm.

EXAMPLE 3

Preparation of Purified FITC-labelled

Albumin Microparticles

Fluorescein isothiocyanate (FITC, Sigma Chemical Company, St. Louis, Mo.) was conjugated to human serum albumin (HSA) in the presence of polymers causing the formation of conjugate particles. Free FITC was washed away from the particles, and the particles redissolved in NaOH yielding FITC-labelled HSA in the absence of free FITC.

Procedure

FITC (6.2 μg) was dissolved in 2 ml of carbonate buffer (pH 10). The dissolved FITC was combined with 1 ml of HSA (25%) and 6 ml of a polymer solution containing 25% PVP and 25% PEG in 0.1 M sodium acetate pH 5.0, while vortexing. The mixture was incubated sequentially at room temperature, 37° C., and 58° C. for 30 minutes each. Conjugate particles were formed. The mixture was centrifuged in a microfuge at 14,000×g, the supernatant removed, and the particles washed three times with deionized water (10 ml each. The particles were resuspended in 10 ml deionized water.

The resuspended particles were visualized in a fluorescence microscope. All fluorescence was associated with the particles. No free fluorescence was observed, indicating that all of the FITC was conjugated to albumin and was not free FITC.

EXAMPLE 4

Release of Radiolabelled Protein and Polymer from Microparticles

Microparticles were prepared using radiolabelled protein (bovine serum albumin, BSA) and radiolabelled polymer (PEG). The release of radioactivity was measured as a function of time.

Microparticles were prepared by combining radiolabelled protein (10 mg/ml $^{14}$C-BSA, NEN, Boston, Mass.) with two volumes of a polymer solution containing 25% PVP (40,000 daltons) and 25% $^3$H-PEG (3,500 daltons, NEN, Boston, Mass.), pH 5.0. The mixture was incubated for 30 minutes at 37° C., 30 minutes at 58° C., and 30 minutes at 70° C. causing the formation of microparticles. The particles were collected by centrifugation.

Protein and polymer were slowly released from the microparticles by adding 500 µl of phosphate buffered saline (pH 7.4) and incubating the mixture at 37° C. while shaking mildly using a Nutator™ rotator. At various time points, particles were precipitated by centrifugation at 8,000 rpm for 10 minutes, the supernatant was removed with a pipette, and radioactivity was assayed by adding liquid scintillation fluid and counting in a liquid scintillation counter. The particles were then resuspended in 500 µl of phosphate buffered saline (pH 7.4) and replaced at 37° C. with gentle rotation until the next time point. The release kinetics of radiolabelled protein and polymer during incubation at 37° C. is shown in FIG. 1.

Microparticles were prepared and assayed for release as described above, however, three different concentrations of polymer were used, and the microparticles were formed by incubation at 58° C. In the first preparation, 25% PEG and 25% PVP were used. In the second preparation, 20% PEG and 20% PVP were used. In the third preparation, 12.5% PEG and 12.5% PVP were used. The release kinetics of radiolabelled protein is shown in FIG. 2. The release kinetics of radiolabelled polymer is shown in FIG. 3.

Figure 4:
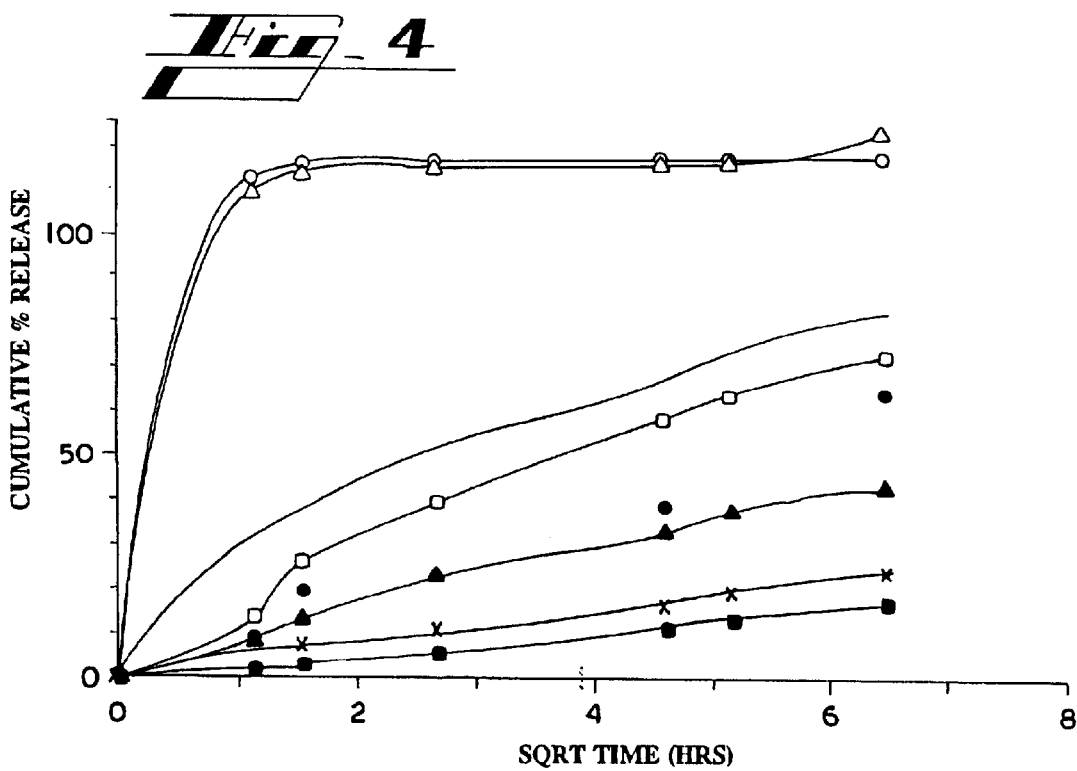
FIG. 4 is a graph showing the cumulative percent of radiolabelled bovine serum albumin (BSA) released from microparticles prepared with three different concentrations of polymer at various incubation temperatures versus the square root of time in hours. The open square symbol represents a total polymer concentration of 25% and incubation at 58° C., the black square symbol represents a total polymer concentration of 25% and incubation at 70° C., the open circle symbol represents a total polymer concentration of 40% and incubation at 58° C., the black circle symbol represents a total polymer concentration of 40% and incubation at 70° C., the open triangle symbol represents a total polymer concentration of 50% and incubation at 58° C., the black triangle symbol represents a total polymer concentration of 50% and incubation at 70° C., the light "X" symbol represents a total polymer concentration of 25% and incubation at 37° C. and 58° C., and the dark "X" symbol represents a total polymer concentration of 25% and incubation at 37° C. and 70° C.

Microparticles were once again prepared and assayed for release as described above, however, three different concentrations of polymer were used, and the microparticles were formed by incubation at 58° C., 70° C., both 37° C. and 58° C., and both 37° C. and 70° C. The release kinetics of radiolabelled protein is shown in FIG. 4. The release kinetics of radiolabelled polymer is shown in FIG. 5. Radiolabelled PEG release as a function of polymer concentration is shown in FIG. 6.

EXAMPLE 5

Formation of DNA-Containing Microparticles

DNA-containing microparticles were prepared and transfected into fibroblast cells. The microparticles were analyzed for transfection efficiency and protein expression.

A 0.025 mL aliquot of a 1 mg/mL solution of a plasmid DNA (pCMVβGal, Promega, Milwaukee, Wis.) was complexed with 0.025 mL of a 5.0 mg/mL solution of poly-L-lysine having an average molecular weight range of from 1 kDa to 40 kDa. (Sigma Chemical Co., St. Louis, Mo.).

To the plasmid DNA-poly-L-lysine complex was added, while vortexing, 0.1 mL of a solution of 25% (weight/volume) polyvinylpyrrolidone (average molecular weight 40 kDa, Spectrum, Gardena, Calif.) and 25% (weight/volume) polyethylene glycol (average molecular weight 3.35 kDa, Spectrum, Gardena, Calif.) in 0.1 M sodium acetate, pH 5.5.

The mixture was incubated at 37° C. for 30 minutes and then at 70° C. for 30 minutes. DNA-containing microparticles were formed. The mixture was centrifuged at 17,500×g for 10 minutes, the supernatant aspirated, and the particles washed three times with 0.3 mL of 10% glycerol (volume/volume) in deionized water. The microparticles were resuspended in 0.050 mL deionized water. The DNA-containing microparticles were applied to NIH3T3 fibroblast cells and incubated up to 24 hours to allow microparticle uptake by the cells. Uptake was terminated by washing the cells three times with phosphate buffered saline (PBS/Ca$^{2+}$+ Mg$^{2+}$-free) (GIBCO-BRL, Gaithersburg, Md.) and the addition of Dulbecco's Minimal Essential Media (DMEM, GIBCO-BRL, Gaithersburg, Md.).

The uptake and expression of the pCMVβGal DNA was assayed for efficiency of transfection and amount of expressed β-galactosidase enzyme. The efficiency of transfection was determined by fixation of the cells and color development with the β-galactosidase enzyme substrate X-Gal (5-bromo-4-chloro-3-indolyl-β-D-galactopyranoside, GIBCO-BRL, Gaithersburg, Md.). The amount of expressed β-galactosidase enzyme was determined by lysing the transfected cells and measuring total enzyme activity with the β-galactosidase enzyme substrate CPRG (chlorphenolred-β-D-galactopyranoside, Boehringer Mannheim, Indianapolis, Ind.)

Results

The amount of expressed β-galactosidase enzyme from lysed cells that were transfected using either: 1) naked DNA (no addition); 2) cationic liposomes plus DNA; or 3) DNA-containing microparticle, prepared as described above, is shown in FIG. 7.

EXAMPLE 6

Formation of Leuprolide Acetate-Containing Microparticles

Microparticles containing leuprolide acetate peptide and human serum albumin were prepared. Leuprolide acetate is a generic analog of leutenizing hormone releasing hormone, which is a peptide used primarily in the treatment of prostate cancer.

A 0.010 mL aliquot of a solution of 10–100 mg/mL leuprolide acetate in water (LHRH, TAP Pharmaceuticals, Deerfield, Ill.) was added to 0.168 mL of a 2–10% (weight/volume) solution of dextran sulfate in water (average molecular weight 500 kDa), and the solution was thoroughly mixed. To the leuprolide/dextran solution was added a 0.856 mL aliquot of a solution containing 25% (weight/volume) polyethylene glycol, having an average molecular weight of 3.35 kDa (Spectrum, Gardena, Calif.), and 25% (weight/volume) polyvinylpyrrolidone, having an average molecular weight of 40 kDa, in an aqueous solution of 0.1 M sodium acetate, pH 5.5. The resulting solution was thoroughly mixed and allowed to stand for up to 30 minutes. A 0.25 mL aliquot of a 20% (weight/volume) solution of human serum albumin (Sigma Chemical Co., St. Louis, Mo.) in water was then added to the solution.

The final solution was thoroughly mixed and placed in a water bath at between 70 and 90° C. for a period of time between 30 minutes and 3 hours. Microparticles were formed.

The microparticles were collected by centrifugation at 17.5K×g for 10 minutes, washed in 0.5 mL of dH$_2$O, and collected again by centrifugation.

Sterile particles were prepared using the foregoing procedure and by sterile filtering all solutions prior to use and conduction all open tube manipulations in a laminar flow tissue culture hood.

In vitro release of leuprolide acetate was measured by centrifugation of microparticles and resuspension in a phosphate buffered saline release medium. The release kinetics are shown in FIG. 8.

The microparticles were composed of approximately 10% leuprolide acetate, 50% human serum albumin, 20% dextran sulfate and 20% polyethylene glycol/polyvinylpyrrolidone.

Similar particles were prepared which also included zinc sulfate or caprylic acid, both of which retarded the release of protein and peptide from the microparticles.

EXAMPLE 7

Preparation of Bovine Serum

Albumin Microparticles Using Polyethylene Glycol and Poloxamer 407

Bovine serum albumin microparticles were prepared using a polymer mixture of polyethylene glycol and poloxamer 407.

1.25 grams of polyethylene glycol (MW 3550, Sigma Chemical Co., St. Louis, Mo.) and poloxamer 407 (BASF, Parsippany, N.J.) were dissolved in 100 ml of a 0.1 N sodium acetate buffer, pH 5.5 to make a 12.5% solution. A solution of 10 mg/ml bovine serum albumin (BSA, Fraction V, Sigma Chemical Co.) was dissolved in $dH_2O$. A 400 ml aliquot of the BSA solution was combined with 800 ml of the polymer solution. The mixture was vortexed. A clear solution formed. The solution was heated to 70° C. for 30 minutes. Particle formation was observed by the presence of a milky white suspension.

The residual polymer solution was removed by centrifugation at 12,500 rpm for 10 minutes and then decanting the solvent. Two washes and centrifugation steps with 10% ethanol in water were performed to remove additional residual polymer.

EXAMPLE 8

Preparation of Bovine Serum

Albumin Microparticles Using Dextran

Bovine serum albumin microparticles were prepared using dextran.

12.5 grams of dextran (MW 500,000, Sigma Chemical Co., St. Louis, Mo.) were dissolved in 100 ml of a 0.1 M sodium acetate buffer, pH 5.0 to make a 12.5% solution. Bovine serum albumin (BSA, Sigma Chemical Co.) was dissolved in $dH_2O$ at a concentration of 10 mg/ml. A 400 ml aliquot of the BSA solution was place in a 1.5 ml microcentrifuge tube. An 800 ml aliquot of the dextran polymer solution was added to the BSA solution. The solution was vortexed. A clear solution formed. The microcentrifuge tube was place in a 70° C. water bath for 30 minutes. A milky white suspension was observed, indicating microparticle formation.

Residual dextran polymer solution was removed by centrifugation at 12,500 rpm for 10 minutes and then decanting the solvent. Two washes and centrifugation steps with 10% ethanol in water were performed to remove additional residual polymer. Scanning electron micrographs revealed the formation of sub-micron sized microparticles often arranged in a string-like structure.

EXAMPLE 9

Preparation of Bovine Serum

Albumin Microparticles Using Eudragit® E100

Bovine serum albumin microparticles were prepared using Eudragit® E100 polymer. This polymer is soluble in an organic solvent that is miscible with water.

Eudragit® E100 polymer (Rohm, Malden, Mass.) was dissolved in a 1:1 solution of 0.1 M sodium acetate buffer (pH 5.0) and ethanol. The final pH of the solution was pH 6.5. A 400 ml aliquot of a 10 mg/ml solution of bovine serum albumin (BSA, Sigma Chemical Co., St. Louis, Mo.) was combined with 800 ml of the Eudragit® E100 polymer solution. A clear solution formed. The BSA/polymer solution was incubated in a 70° C. water bath for 30 minutes. A milky white suspension was observed, indicating microparticle formation. The particles were collected by centrifugation for 10 minutes at 8,000 rpm and decantation of the liquid.

EXAMPLE 10

Preparation of Insulin Microparticles Using Dextran

Insulin microparticles were prepared using dextran polymer.

A 20% (weight/weight) solution of dextran polymer (MW 500,000, Sigma Chemical Co., St. Louis, Mo.) was dissolved in pH 5.0 sodium acetate buffer. 1.9 ml of $dH_2O$ was added to 20.5 mg of insulin (Sigma Chemical Co.). 100 ml of 0.2 M HCl was added to dissolve the insulin. A 400 ml aliquot of the insulin solution was placed in a test tube. An 800 ml aliquot of the dextran solution was added to the insulin solution. The mixture was vortexed. The mixture turned cloudy upon addition of the dextran solution. The tubes were heated to a final temperature of either 70° C. or 90° C. to form insulin microparticles. The microparticles were centrifuged at 10,000 rpm for 5 minutes and the liquid decanted to remove residual polymer. The microparticles were washed with 10% ethanol in water.

The microparticles were place in a phosphate buffered saline solution, pH 7.4 to determine the dissolution characteristics. The insulin particles formed at a final temperature of 90° C. did not dissolve in the phosphate buffered saline whereas the insulin particles prepared at a final temperature of 70° C. dissolved within 15 minutes. Therefore, insulin particle stability may be adjusted by varying the incubation temperature employed during particle formation.

EXAMPLE 11

Preparation of Microparticles Using

Various Polymers

Human serum albumin microparticles were prepared using nine different polymers or mixtures of polymers.

Procedure

A protein solution (1–5% human serum albumin, pH 4.5–5.5 or bovine serum albumin) in a buffer was prepared.

The following polymer solutions were prepared:

polyethylene glycol/polyvinylpyrrolidone (3 kDa PEG/40 kDa PEG in a 1:1 mixture)

hetastarch (500 kDa)
Pluronic L-101™ polymer
dextran (3–500 kDa)
dextran sulfate (3–500 kDa)
polyvinylpyrrolidone (10–360 kDa)
polyethylene glycol/polyvinylpyrrolidone with inulin (a polysaccharide)
polyethylene glycol/polyvinylpyrrolidone with Pluronic L-101™ polymer
dextran with Pluronic L-101™ polymer Approximately one volume of protein solution was mixed with two volumes of polymer solution. The mixture was incubated in a water bath at 70 to 90° C. for thirty minutes. The mixture was then placed in an ice bath. Microparticle formation was observed.

The microparticles were centrifuged until compacted into a pellet, the supernatant decanted, and the pellet washed twice in a 10% ethanol in water solution to remove the residual polymer solution. Microparticles were then washed three times with deionized water. The microparticles were used or tested immediately or were lyophilized for subsequent use.

Observations

Microparticles prepared using polymers having a higher molecular weight or a higher concentration of polymers provide a more viscous medium which produced a more uniform microparticle size distribution. The inclusion of a surfactant, such as Pluronic L-101™ polymer or mixing during microparticle formation affected microparticle size. An increase in protein concentration during microparticle formation caused an increase in the incorporation of protein into the microparticles. An increase in polymer size generally caused an increase in protein incorporation into the microparticles. The use of different polymers affected release kinetics. For example bovine serum albumin (BSA) microparticles prepared using dextran released approximately 15% less BSA than microparticles prepared using PEG/PVP. However, the release of polysaccharide from protein-polysaccharide microparticles, such as the release of $^3$H-inulin from human serum albumin/inulin microparticles, was more rapid when dextran rather than PEG/PVP was employed.

EXAMPLE 12

Preparation of Protein Microparticles Containing

Nafarelin Acetate Using Various Polymers

Protein microparticles containing the drug nafarelin acetate were prepared. Nafarelin acetate is useful in the treatment of endometriosis, precocious puberty and prostate cancer.

Procedure

Human serum albumin microparticles were prepared as described above in Example 11 using nine different polymers or mixtures of polymers. Nafarelin acetate (Roche Laboratories, Nutley, N.J.) was dissolved in deionized water to produce a 10 mg/ml solution.

To 1 mg of nafarelin acetate was added 10 mg of the human serum albumin microparticles. The mixture was vortexed and mixed for 16 hours at 4° C. A 3 M ammonium sulfate solution was added to the mixture to a final concentration of 0.5 M and vortexed and mixed for 15 minutes at ambient temperature. A 1 M zinc sulfate solution was added to a final concentration of either 0.01 M, 0.1 M or 1 M and vortexed and mixed for 1 hour at ambient temperature.

The mixtures were centrifuged, supernatant decanted and pellet resuspended in deionized water three times to wash the microparticles.

Observations

The addition of zinc sulfate reduced the rate of release of nafarelin acetate from human serum albumin microparticles. The results are shown in FIG. 9.

EXAMPLE 13

Preparation of Doxorubicin/Albumin

Microparticles

Human serum albumin microparticles containing the chemotherapeutic drug doxorubicin were prepared.

To 1 mL of a solution of 250 mg/mL human serum albumin (Sigma, St. Louis, Mo.) in $dH_2O$ was added 0.05 mL of a 5 mg/mL solution of doxorubicin (Sigma Chemical Co., St. Louis, Mo.) in $dH_2O$, the combined solution was mixed and allowed to stand at room temperature for 30 minutes. To the above solution was added 3.0 mL of a solution of 200 mg/mL dextran sulfate (MW 500,000, Sigma Chemical Co., St. Louis, Mo.) in $dH_2O$, and the resulting solution was mixed and incubated at 37° C. for 30 minutes. The solution was then incubated at 70° C. for 30 minutes, after which 1.0 mL of 3.0 M sodium acetate, pH 5.0, was added and the resulting solution mixed. The solution was then incubated at 90° C. for 30 minutes. Microparticles were formed. The microparticles were washed two times with 5.0 mL $dH_2O$.

EXAMPLE 14

Incorporation of LHRH into

Dextran Sulfate/Albumin Microparticles

Luteinizing hormone releasing hormone was incorporated into microparticles composed of human serum albumin and dextran sulfate microparticles.

To 0.168 mL of a 10% (weight/volume) solution of dextran sulfate (average MW 500,000, Sigma Chemical Co., St. Louis, Mo.) in $dH_2O$ was added 0.25 mL of a 20% (weight/volume) solution of human serum albumin (Sigma Chemical Company, St. Louis, Mo.) in $dH_2O$. The solution was thoroughly mixed, and 0.856 mL of a solution of 25% (weight/volume) polyethylene glycol (average MW 3.35 kDa, Spectrum, Gardena, Calif.) and 25% (weight/volume) polyvinylpyrrolidone (average MW 40 kDa, Spectrum, Gardena, Calif.) in an aqueous solution of 0.1 M sodium acetate, pH 5.5 was added.

The resulting solution was thoroughly mixed and placed in a water bath at a temperature between 70 and 90° C. for between 30 minutes and 3 hours. Microparticles were formed.

Microparticles were collected by centrifugation at 17.5K×g for 10 minutes, resuspended for washing in 0.5 mL of $dH_2O$, and collected again by centrifugation. The microparticles were resuspended in 0.3 mL of a solution of 0.1 M sodium acetate, pH 5.5. A 0.01 mL aliquot of a 10 mg/mL solution of luteinizing hormone releasing hormone (LHRH, Sigma Chemical Co., St. Louis, Mo.) in $dH_2O$ was added and incubated for 16 hours at room temperature to allow the LHRH peptide to bind to the microparticles. After the 16 hour binding incubation, the unbound LHRH peptide was removed by two cycles of washes with $dH_2O$ and collection by centrifugation. The yield of LHRH incorporation was typically 83 to 90%.

Modifications and variations of the present microparticle compositions and methods of production and use will be obvious to those skilled in the art from the foregoing detailed description. Such modifications and variations are intended to come within the scope of the appended claims.

We claim:

1. A microparticle comprising macromolecule and polymer, wherein the concentration of macromolecule in the microparticle is at least 40% and less than 100% by weight.

2. A microparticle comprising a macromolecule and a polymer, wherein said macromolecule is a hormone, and said polymer is a water soluble, linear or branched high molecular weight polymer capable of removing water from the macromolecule.

3. The microparticle of claim 2 wherein the polymer is selected from the group consisting of polyvinylpyrrolidone, polyethylene glycol, dextran, nonylphenol ethoxylates, polyvinyl alcohol, and mixtures thereof.

4. The microparticle of claim 3 wherein the polymer is a mixture of polyvinylpyrrolidone and polyethylene glycol.

5. A method of preparing a microparticle comprising combining a hormone and a water soluble, linear or branched high molecular weight polymer in an aqueous solution, and heating the peptide hormone and polymer for a sufficient period of time to form microparticles.

6. The method of claim 5 wherein the polymer is selected from the group consisting of polyvinylpyrrolidone, polyethylene glycol, dextran, nonylphenol ethoxylates, polyvinyl alcohol, and mixtures thereof.

7. The method of claim 6 wherein the polymer is a mixture of polyvinylpyrrolidone and polyethylene glycol.

8. The method of claim 5 wherein the hormone and polymer are heated at a temperature in the range of from about 37° C. to about 90° C., for 5 minutes to 2 hours.

9. The method of claim 8 wherein the peptide hormone and polymer are heated at a temperature in the range of from about 50° C. to about 90° C., for 5 minutes to 30 minutes.

10. A microparticle prepared by the method of claim 5.

* * * * *